(12) United States Patent
Spudich et al.

(10) Patent No.: US 6,960,457 B1
(45) Date of Patent: Nov. 1, 2005

(54) REVERSIBLE IMMOBILIZATION OF ARGININE-TAGGED MOIETIES ON A SILICATE SURFACE

(75) Inventors: James A. Spudich, Palo Alto, CA (US); Steffen Nock, Waldronn (DE); Peter Wagner, Heilbronn (DE)

(73) Assignee: Stanford University, Palo Alto, CA (US)

( * ) Notice: Subject to any disclaimer, the term of this patent is extended or adjusted under 35 U.S.C. 154(b) by 0 days.

(21) Appl. No.: 09/486,480

(22) PCT Filed: Sep. 3, 1998

(86) PCT No.: PCT/US98/18531

§ 371 (c)(1),
(2), (4) Date: Oct. 25, 2000

(87) PCT Pub. No.: WO99/12036

PCT Pub. Date: Mar. 11, 1999

Related U.S. Application Data
(60) Provisional application No. 60/057,929, filed on Sep. 4, 1997.

(51) Int. Cl.[7] .................. C12N 11/14; G01N 33/531; G01N 33/552; G01N 33/551; C07K 1/00
(52) U.S. Cl. .................. 435/176; 435/961; 436/527; 436/524; 436/535; 436/518; 436/543; 530/810; 530/811; 530/816; 530/807; 530/402
(58) Field of Search .................. 436/172, 518, 436/527–524, 543; 435/176, 961; 530/350, 300, 324–331, 402, 806, 807, 810, 811

(56) References Cited

U.S. PATENT DOCUMENTS

| | | | |
|---|---|---|---|
| 4,029,756 A | * 6/1977 | Gaafar ............................ 424/1 |
| 4,239,519 A | 12/1980 | Beall et al. ...................... 65/2 |
| 4,297,139 A | 10/1981 | Beall et al. ...................... 65/2 |
| 4,338,094 A | * 7/1982 | Elahi ............................ 23/230 |
| 4,339,540 A | 7/1982 | Beall et al. ...................... 65/2 |
| 4,366,241 A | 12/1982 | Tom et al. ...................... 435/7 |
| 4,376,110 A | 3/1983 | David et al. ................. 436/513 |
| 4,448,715 A | 5/1984 | Ryan et al. ................. 260/112 |
| 4,511,503 A | 4/1985 | Olson et al. ............ 260/112 R |
| 4,517,288 A | 5/1985 | Giegel et al. ................... 435/7 |
| 4,542,225 A | 9/1985 | Blattler et al. .............. 548/473 |
| 4,545,985 A | 10/1985 | Pastan et al. ................. 424/85 |
| 4,569,789 A | 2/1986 | Blattler et al. ............. 530/391.9 |
| 4,589,071 A | 5/1986 | Yamamuro et al. ...... 364/424.1 |
| 4,614,714 A | * 9/1986 | Kusakabe et al. ............. 435/25 |
| 4,618,492 A | 10/1986 | Blattler et al. ................ 424/85 |
| 4,625,014 A | 11/1986 | Senter et al. ................ 530/300 |
| 4,629,713 A | * 12/1986 | Suzuki et al. .................. 502/84 |
| 4,659,839 A | 4/1987 | Nicolotti et al. ............. 548/546 |
| 4,671,958 A | 6/1987 | Rodwell et al. .............. 424/85 |
| 4,680,338 A | 7/1987 | Sundoro |
| 4,683,202 A | 7/1987 | Mullis ......................... 435/91 |
| 4,699,784 A | 10/1987 | Shih et al. ................... 424/85 |
| 4,837,168 A | 6/1989 | de Jaeger et al. |
| 4,880,911 A | * 11/1989 | Brewer et al. ............... 530/351 |
| 4,894,443 A | 1/1990 | Greenfield et al. ......... 530/388 |
| 5,010,175 A | 4/1991 | Rutter et al. ................ 530/334 |
| 5,017,478 A | 5/1991 | Cashion et al. ............ 435/69.1 |
| 5,177,005 A | * 1/1993 | Lloyd et al. ................... 435/94 |
| 5,230,998 A | * 7/1993 | Neurath et al. .............. 435/7.1 |
| 5,288,514 A | 2/1994 | Ellman ......................... 427/2 |
| 5,405,766 A | * 4/1995 | Kallury et al. .............. 435/174 |
| 5,532,142 A | 7/1996 | Johnston et al. ........... 435/69.1 |
| 5,536,382 A | 7/1996 | Sunzeri ...................... 204/451 |
| 5,539,082 A | 7/1996 | Nielsen et al. ............. 530/300 |
| 5,539,083 A | 7/1996 | Cook et al. ................. 530/333 |
| 5,541,061 A | 7/1996 | Fodor et al. ................... 435/6 |
| 5,549,974 A | 8/1996 | Holmes ....................... 428/403 |
| 5,559,410 A | 9/1996 | Papazian et al. ............ 318/445 |
| 5,561,045 A | * 10/1996 | Dorval et al. .................. 435/5 |
| 5,569,588 A | 10/1996 | Ashby et al. .................. 435/6 |
| 5,576,220 A | 11/1996 | Hudson et al. ............. 436/518 |
| 5,585,639 A | 12/1996 | Dorsel et al. ............ 250/458.1 |
| 5,593,853 A | 1/1997 | Chen et al. .................. 435/29 |
| 5,874,668 A | * 2/1999 | Xu et al. ...................... 73/105 |
| 5,993,769 A | * 11/1999 | Pinnavaia et al. .......... 423/331 |
| 6,107,060 A | * 8/2000 | Keeling et al. ............. 435/69.7 |
| 6,319,668 B1 | * 11/2001 | Nova et al. .................... 435/6 |
| 6,379,903 B1 | * 4/2002 | Brizzard et al. ............. 435/7.1 |
| 6,468,759 B1 | * 10/2002 | Charych ..................... 435/7.4 |

FOREIGN PATENT DOCUMENTS

| | | |
|---|---|---|
| EP | 0 188256 | 8/1991 |
| EP | 0 246 864 | 7/1994 |
| GB | 2306484 | * 5/1997 |
| JP | 356152741 A | * 11/1981 |
| WO | WO 91/19735 | 12/1991 |
| WO | WO 92/00091 | 1/1992 |
| WO | WO 93/20242 | 10/1993 |
| WO | WO 97/00271 | 1/1997 |

OTHER PUBLICATIONS

Koennecke et al. Monatsh. Chem. 113: 331–337, 1982.*
Sassenfeld et al. Biotechnology 2: 76–81, 1984.*
Mueller et al. Biophys. J. 68: 1681–1686, 1995.*
Hirabayashi et al. J. Mol. Recog. 3: 204–207, 1990.*
Porath et al. (1975) "Metal chelate affinity chromatography, a new approach to protein fractionation," Nature 258:598–599.
Collioud et al. (1993) "Oriented and Covalent Immobilization of Target Molecules to Solid Supports: Synthesis and Application of a Light–Activatable and Thiol–Reactive Cross–Linking Reagent," Bioconjugate Chem. 4:528–536.
Schuhmann et al. (1991) "Immobilization of Enzymes on Langmuir–Blodgett Films via a Membrane–Bound Receptor. Possible Applications for Amperometric Biosensors," Adv. Mater. 3:388–391.

(Continued)

*Primary Examiner*—S. Devi
(74) *Attorney, Agent, or Firm*—Medlen & Carroll LLP

(57) ABSTRACT

This invention provides materials and methods for the site specific attachment of virtually any moiety to a layered silicate surface. The methods involve covalently attaching the moiety to an arginine tag; and contacting the arginine tag with the layered silicate (e.g., mica) surface.

9 Claims, 4 Drawing Sheets

OTHER PUBLICATIONS

Lu et al. (1995) "Oriented Immobilization of Fab' Fragments on Silica Surfaces," Anal. Chem. 67:83–87.

Iwane et al. (1997) "Myosin Subragment–1 Is Fully Equipped with Factors Essential for Motor Function," Biophys. Biochem. Res. Comm. 230:76–80.

Ng et al. (1995) "Engineering Protein—Lipid Interactions: Targeting of Histidine–Tagged Proteins to Metal–Chelating Lipid Monolayers," Langmuir 11:4048–4055.

Schmitt et al. (1996) Specific Proteins Docking to Chelator Lipid Monolayers Monitored by FT–IR Spectroscopy at the Air–Water Interface Agnew. Chem. Int. Ed. Engl. 35:317–320.

Frey et al. (1996) "Two–dimenstional protein crystallization via metal–ion coordination by naturally occurring surface histidines," Proc. Natl. Acad. Sci. USA 94:4937–4941.

Kubalek et al. (1994) "Two–Dimensional Crystallization of Histidine–Tagged, HIV–1 Reverse Transcriptase Promoted by a Novel Nickel–Chelating Lipid," J. Struct. Biol. 113:117–123.

Sigal et al. (1996) "A Self–Assembled Monolayer for the Binding and Study of Histidine–Tagged Proteins by Surface Plasmon Resonance," Anal. Chem. 68:490–497.

Zahn et al. (1993) "Two–dimensional Crystals of the Molecular Chaperone GroEL Reveal Structural Plasticity," J. Mol. Biol. 229:579–584.

Yang et al. (1994) "Strucutre and stability of pertussis toxin studied by in situ atomic force microscopy," FEBS Lett. 338:89–92.

Guckenberger et al. (1994) "Scanning Tunneling Microscopy of Insulators of Biological Specimens Based on Lateral Conductivity of Ultrathin Water Films," Science 266:1538–1540.

Müller et al. (1996) "Immuno–Atomic Force Microscopy of Purple Membrane," Biophys. J. 70:1796–1802.

Woodward et al. (1996) "In Situ Observation of Self–Assembled Monolayer Growth," J. Am. Chem. Soc. 118:7861–7862.

Schwartz et al. (1992) "Growth of a Self–Assembled Monolayer by Fractal Aggregation," Phys. Rev. Lett. 69:3354–3357.

Okusa et al. (1994) "Chemical Modification of Molecularly Smooth Mica Surface and Protein Attachment," Langmuir 10:3577–3581.

Hu et al. (1996) "Imaging of Single Extendedf DNA Molecules on Flat (Aminopropyl)triethoxysilane–Mica by Atomic Force Microscopy," Langmuir 12:1697–1700.

Xiao et al. (1996) "Chain Length Dependence of the Frictional Properties of Alleysilane Molecules Self–Assembled on Mica Studied by Atomic Force Microscopy," Langmuir 12:235–237.

Britt et al. (1996) "An AFM Study of the Effects of Silanization Temperature, Hydration, and Annealing on the Nucleation and Aggregation of Condensed OTS Domains on Mica," J. Colloid Interface Sci. 178:775–784.

Shelden et al. (1993) "Ion Exchange on Muscovite Mica with Ultrahigh Specific Surface Area," J. Colloid Interface Sci. 157:318–327.

Hähner et al. (1996) "orientation and electronic structure of methylene blue on mica: A near edge x–ray absorption fine structure spectroscopy study," J. Chem. Phys. 104:7749–7757.

Sharma et al. (1996) "Characterization of Adsorbed Ionic Surfactants on a Mica Substrate," Langmuir 12:6506–6512.

Eriksson et al. (1996) "Equilibrium Wetting Studies of Cationic Surfactant Adsorption on Mica, 1. Mono– and Bilayer Adsorption of CTAB," J. Colloid Interface Sci. 181:476–489.

Hansma et al. (1995) "Applications for Atomic Force Microscopy of DNA," Biophys. J. 68:1672–1677.

Shelden et al. (1994) "Nanophase molecular droplets: individual polystyrene molecules of mica imaged with scanning electron and atomic–force microscopoy," Polymer 35:1571–1575.

Spudich (1994) "How molecular motors work," Nature 372:515–518.

Borlinghaus et al. (1987) "Radiosensitizer Conjugation to the Carcinoma 19–9 Monoclonal Antiobdy," Cancer Res. 47:4071–4075.

Thorpe et al. (1982) in *Monoclonal Antibodies in Clinical Medicine* Academic Press, pp. 168–190.

Waldmann (1991) "Monoclonal Antibodies in Diagnosis and Therapy," Science 252:1657.

Barany and Merrifield, *Solid–Phase Peptide Synthesis*, pp. 3–284 in *The Peptides: Analysis, Synthesis, Biology, vol. 2: Special Methods in Peptide Synthesis, Part A.*

Merrifield et al. (1963) "Solid Phase Peptide Synthesis, I. The Synthesis of a Tetrapeptide," J. Am. Chem. Soc. 85:2149–2156.

Stewart et al., Solid Phase Peptide Synthesis, 2nd ed., Pierce Chem. Co., Rockford, IL, 1984.

Beaucage et al., (1981) "Deoxynucleoside Phosphoramidites—A New Class of Key Intermediates for Deoxypolynucleotide Synthesis," Tetra. Lett. 22:1859–1862.

Matteucci et al. (1981) "Synthesis of Deoxyliogonucleotides on a Polymer Support," J. Am. Chem. Soc. 103:3185.

Berger and Kimmel, Guide to Molecular Cloning Techniques, Methods in Enzymology, vol. 152, Academic Press, Inc., San Diego, CA.

Sambrook et al. (1989) *Molecular Cloning, A Laboratory Manual, 2nd ed.*, vol. 1–3, Cold Spring Harbor Laboratory, Cold Spring Harbor Press, NY.

*Current Protocols in Molecular Biology*, F. M. Ausubel et al., eds., Current Protocols, a joint venture between Greene Publishing Associates, Inc. and John Wiley & Sons, Inc., (1994 Supplement).

Innis et al. (1990) *PCR Protcols, A Guide to Methods and Applications*, Academic Press Inc., San Diego, CA.

Kwoh et al.(1989) "Transcription–based amplification system and detection of amplified human immunodeficiency virus type 1 with a bead–based sandwich hybridization format," Proc. Natl. Acad. Sci. USA 86:1173.

Guatelli et al. (1990) "Isothermal, in vitro amplification of nucleic acids by a multienzyme reaction modeled after retroviral replication," Proc. Natl. Acad. Sci. USA 87:1874.

Lomell et al. (1989) "Quantitative Assays Based on the Use of Replicatable Hybridization Probes," J. Clin. Chem. 35:1826.

Landegren et al. (1988) "A Ligase–Mediated Gene Detection Technique," Science 241:1077–1080.

Van Brunt (1990) "Amplifying Genes: PCR and Its Alternatives," Bio/Technology 8:291–294.

Wu and Wallace (1989) Wu and Wallace, "The Ligation Amplification Reaction (LAR)—Amplification of Specific DNA Sequences Using Sequential Rounds of Template–Dependent Ligation," Genomics 4:560.

Barringer et al. (1990) "Blunt–end and single–strand ligations by *Esherichia coli* ligase: influence on an in vitro amplification scheme," Gene 89:117.

Yanofsky (1984) "Repression Is Relieved Before Attenuation in the trp Operon of *Escherichia coli* as Tryptopham Starvation Becomes Increasingly Server," J. Bateriol. 158:1018–1024.

Herskowitz et al. (1980) "The Lysis–Lysogeny Decisionof Phage λ: Explicit Programming and Responsiveness," Ann. Rev. Genet. 14:399–445.

Sherman et al. (1982) Methods in Yeast Genetics, Cold Spring Harbor Laboratory, Cold Spring Harbor, NY.

Wahleithner et al. (1991) "Expression and assembly of spectrally active recombinant holophytochrome," Proc. Natl. Acad. Sci. USA 88:10387–10391.

Murphy and Lagarias (1997) "Purification and Chracterization of Recombinant Affinity Peptide–Tagged Oat Phytochrome A," Photochem. Photobiol. 65:750–758.

Wu et al. (1996) "The methylotrophic yeast *Pichi pastoris* synthesizes of functionally active chromophore precursor of the plant photoreceptor phytochrome," Proc. Natl. Acad. Sci. USA 93:8989–8994.

Botstein et al., (1979) "Sterile Host Yeasts (SHY): A Eukaryotic System of Biological Containment for Recombinant DNA Experiments," Gene 8:17–24.

Broach et al. (1979) "Transformation in Yeast: Development of a Hybrid Cloning Vector and Isolation of the CANI Gene," Gene 8:121–133.

Paszkowski et al. (1984) "Direct gene transfer to plants," Embo. J. 3:2717–2722.

Fromm et al. (1985) "Expression of genes transferred into monocot and dicot plant cells by electroporation," Proc. Natl. Acad. Sci. USA 82:5824.

Klein et al. (1987) "High–velocity microprojectiles for delivering nucleic acids into living cells," Nature 327:70–73.

Fisk et al. (1993) "The introduction and expression of transgenes in plants," Scientia Horticulturae 55:5–36.

Potrykus (1990) "Gene transfer methods for plants and cell cultures," CIBA Found. Symp. 154:198.

Horsch et al. (1984) "Inheritance of Functional Foreign Genes in Plants," Science 233:496–498.

Fraley et al. (1983) "Expression of bacterial genes in plant cells," Proc. Natl. Acad. Sci. USA 80:4803.

Hooykaas (1989) "Transformation of plant cells via Agrobactierum," Plant Mol. Biol. 13:327–336.

Bechtold et al. (1993) "*In planta Agrobacterium* mediated gene transfer by infiltration of adult *Arabidopsis thaliana* plants," Comptes Rendus De L Academic Des Sciences Serie Iii–Sciences De La Vie–Life Sciences 316:1194–1199.

Valvekens et al. (1988) "*Agrocbacterium tumefaciens*–mediated transformation of Arabidopsis thalian a root explants by using kanmycin selection," Proc. Natl. Acad. Sci. USA 85:5536–5540.

de la Peria et al. (1987) "Transgenic rye plants obtained by injecting DNA into young floral tillers," Nature 325:275–276.

Rhodes et al. (1988) "Genetically Transformed Maize Plants from Protoplasts," Science 240:204–207.

Shimamoto et al. (1989) "Fertile transgenic rice plants regenerated from transformed protoplasts," Nature 338:274–276.

Shuerman et al. (1993) "Transformation of temperate woody crops: Progress and potentials," Scientia Horticulturae 55:101–124.

James et al. (1989) "Genetic transformation of apple (*Malus pumila* Mill.) using a disarmed Ti–binary vector," Plant Cell. Rep. 7:658–661.

Evans et al. (1983), pp. 124–176 ini *Protoplasts Isolation and Culture, Handbook of Plant Cell Culture*, MacMillan Publishing Company, NY.

Binding, Regeneration of Plants in Plant Protoplasts, pp. 21–37 CRC Press, Boca Raton, FL, 1985.

Klee et al. (1987) "Agrobacterium–Mediated Plant Transformation and Its Further Applications to Plant Biology," Ann. Rev. Plant Physiol. 38:467–86.

Berman et al. (1983) "Detection of Antibodies to Herpes Simplex Virus with a Continuous Cell Line Expressing Cloned Glycoprotein D," Science 222:524–527.

Thomsen et al. (1984) "Promoter–regulatory region of the major immediate early gene of hyman cytomegalovirus," Proc. Natl. Acad. Sci. 81:659–663.

Brinster et al. (1982) "Regulation of metallothionein–thymidine kinase fusion plasmids injected into mouse eggs," Nature 296:39–42.

Gallop et al. (1994) "Applications of Combinatorial Technologies to Drug Discovery. 1. Background and Peptide Combinatorial Libraries," J. Med. Chem. 37(9):1233–1251.

Fuka (1991) "General method for rapid synthesis of multicomponent peptide mixutures," Int. J. Pept. Prot. Res.37:487–493.

Houghten et al. (1991) "Generation and use of synthetic peptide combinatorial libraries for basic research and drug discovery," Nature 354:84–88.

Hagihara et al. (1992) "Vinylogous Polypeptides: An Alternative Peptide Backbone," J. Amer. Chem. Soc. 114:6568.

Hirschmann et al. (1992) "Nonpeptidal Peptidomimetics with a β–D–Glucose Scaffolding: A Partial Somatostatin Agonist Bearing a Clos Structural Relationship to a Potent, Selective Substance P Antagonist," J. Amer. Chem. Soc. 114:9217–9218.

Chen et al. (1994) "Analogous" Organic Synthesis of Small-Compound Libraries: Validation of Combinatorial Chemistry in Small–Molecular Synthesis, J. Amer. Chem. Soc. 116:2661.

Cho et al. (1993) "An Unnatural Biopolymer," Science 261:1303.

Campbell et al. (1994) "Phosphonate Ester Synthesis Using a Modified Mitsunobu Condensation," J. Org. Chem. 59:658.

Gordon et al. (1994) "Application of Combinatorial Technologies to Drug Discovery. 2. Combinatorial Prgamoc Synthesi, Library Screening Strategies, and Future Directions." J. Med. Chem. 37:1386.

Vaughan et al. (1996) "Human Antibodies with Sub–nanomolar Affinities Isolated from a Large Non–immunized Phage Display Library," Nature Biotechnology 14(3):309–314.

Liang et al. (1996) "Parallel Synthesis and Screening of a Solid Phase Carbohydrate Library," Science 274:1520–1522.

Baum (1993) "Solid–phase synthesis of benzodiazepines," C&EN, Jan. 18, pp. 33–34.

Gittes et al. (1996) "Directional Loading of the Kinesin Motor Molecule as it Buckles a Microtubule," Biophys. J. 70(1):418–29.

Shirakawa et al. (1995) "The Mode of ATP–Dependent Microtubule–kinesin Sliding in the Auxotonic Condition," J. Exp. Biol. 198:1809–15.

Vale and Kreis, 1993, Guidebook to the Cytoskeletal and Motor Proteins, NY, Oxford University Press.

Goldstein (1993) "With Apologies to Scheherazade: Tails of 1001 Kinesin Motors," Ann. Rev. Genetics 27:319–351.

Mooseker and Cheney (1995) "Unconventional Myosins," Annu. Rev. Cell Biol. 11:633–675.

*Methods in Cell Biology, vol. 37: Antibodies in Cell Biology*, David J. Asai, ed., Academic Press, Inc., NY, 1993.

Stites and Terr (1991) in *Basic and Clinical Immunology*, 7th ed., Appleton & Lange, Norwalk, Connecticut.

Chalfie et al. (1994) "Green Fluorescent Protein as a Marker for Gene Expression," Science 263:801–805.

Yang et al. (1996) "The molecular structure of green fluorescent protein," Nature Biotechnology 14:1246–1251.

Nock et al. (1997) "Reversible, site–specific immobilization of polyarginine–tagged fusion proteins on mica surfaces," FEBS Letters 414:233–238.

Wagner et al. (1997) "Bioreactive self–assembled monolayers on hydrogen–passivated Si (III) as a new class of atomically flat substrates for biological scanning probe microscopy," J.Struct. Biol. 119:189–201.

Spudich et al. (1996) "Effect of different surfaces and binding modes on the velocity of a single–headed myosin fragment in the vitro motility assay," Mol. Biol. of the Cell 7:35a, Abstract 206.

Hirabayashi et al. (1992) "Arginine–tail method, an affinity tag procedure utilizing anhydrotrypsin agarose," J. Chromatogr. 597:181–187.

Geke et al. (1997) "Ion exchange of cation–terminated poly(ethylene oxide) chains of mica surfaces," J. Colloid. Interface Sci. 189:283–287.

* cited by examiner

MGSSHHHHHHSSGLVPRGSH | GFPH6 |

MGSSHHHHHHSSGLVPRGSRRRRRRH | GFPH6R6 |

MGSSHHHHHHSSGLVPRGSH | GFPR6 | GTARRRRRR

US 6,960,457 B1

REVERSIBLE IMMOBILIZATION OF ARGININE-TAGGED MOIETIES ON A SILICATE SURFACE

CROSS-REFERENCE TO RELATED INVENTIONS

This Application is the U.S. national stage entry of, and claims priority to PCT/US98/18531, filed Sep. 3, 1998, now abandoned, which claims priority to Provisional Patent Application Ser. No. 60/057,929, filed on Sep. 4, 1997, now abandoned, which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with the Government support under Contract Numbers GM33289 and GM40509, awarded by the National Institutes of Health. The Government of the United States of America may have certain rights in this invention.

BACKGROUND OF THE INVENTION

The immobilization of functional proteins on flat surfaces is of crucial importance for studying their interaction with ligands and examining their structure by means of electron and scanning probe microscopy and other biophysical techniques requiring a solid interface. Targeting proteins at specific sites and anisotropically immobilizing them on a surface while preserving their functionality is a major precondition to facilitate biochemical recognition and interaction, to present selected sites for structural investigation, to induce two-dimensional crystallization, and to develop new biosensors and supramolecular assemblies.

Generally, two methods have been used to attach (immobilize) proteins to a solid surface. In the first method, the peptide is applied to the surface in solution, which is then evaporated off, leaving the peptide dried to the surface. Such non-specific attachment is inefficient for small peptides and applicable only to methods which do not require a large concentration of immobilized peptide, as much will be resolubilized subsequently in the presence of solution. Moreover, because the attachment is non-specific, peptides will be attached in random and variant orientations. Where presentation of a particular active site is critical, such variance can further reduce the specificity of the bound peptide.

In the more common two-step chemical coupling process, the solid surface is first passively coated with a large protein, such as an immunoglobulin or bovine serum albumin. Then, a hetero-bifunctional cross-linking agent, such as SPDP or glutaraldehyde, is attached to the protein and used to capture peptide from solution. Such a method, while time consuming, is currently used, for example, in cell culture procedures which require a high concentration of bound peptide. While this typically results in higher quantities of bound protein, because a protein may contain numerous sites capable of interacting, peptides will be attached in random and variant orientations. Where presentation of a particular active site is critical, such variance can further reduce the specificity of the bound peptide with the cross-linker. In addition it is often difficult or impossible to remove from the underlying surface.

An alternative technique for binding proteins has been used for protein purification. This method, named "Immobilized Metal Affinity Chromatography" (IMAC) resulted from the recognition that certain proteins have an affinity for heavy metal ions, which could be an additional distinguishing feature to use in attempting separation of the proteins. This feature applies especially to proteins containing histidine or cysteine residues, which have been found to complex with chelated zinc or copper ions and become adsorbed on a chelating resin (Porath et al. (1975) Nature, 258: 598–99 (1975). Again, this method suffers the deficiency that it requires a metal cation coordinated to a surface which is difficult to produce in an atomically smooth form. In addition, metals are toxic to a number of biological processes limiting their efficacy in assays requiring biological activity of one or more components. Finally, the orientation of proteins on metal surfaces is difficult to control.

Several efforts have been made to immobilize proteins with controlled orientation either covalently utilizing single reactive thiol groups of cysteine residues (Colliuod et al. (1993) Bioconjugate Chem. 4, 528–536 ), or non-covalently, but specifically via immobilized antibodies (Schuhmann et al. (1991) Adv. Mater. 3: 388–391; Lu et al. (1995) Anal. Chem. 67: 83–87), the biotin/streptavidin system (Iwane et al. (1997) Biophys. Biochem. Res. Comm. 230: 76–80), or metal-chelating Langmuir-Blodgett films (Ng et al. (1995) Langmuir 11: 4048–4055; Schmitt et al. (1996) Angew. Chem. Int. Ed. Engl. 35: 317–320; Frey et al. (1996) Proc. Natl. Acad. Sci. USA 93: 4937–4941; Kubalek et al. (1994) J. Struct. Biol., 113: 117–123) and metal-chelating self-assembled monolayers (Sigal et al. (1996) Analytical Chem., 68: 490–497) for binding of polyhistidine fusion proteins. Mica, with the ideal structure $KAl_2[AlSi_3O_{10}](OH,F)_2$, refers to a group of layered aluminosilicate minerals whose crystals exhibit a large degree of basal cleavage, allowing them to be split into very thin atomically flat sheets.

Due to its flatness and hydrophilic surface, mica has been established as a standard substrate for electron and scanning probe microscopy applications (see e.g., Zahn et al. (1993) J. Mol. Biol., 229: 579–584; Yang et al. (1994) FEBS Lett. 338: 89–92; Guckenberger et al. (1994) Science 266: 1538–1540; Mueller et al. (1996) Biophys. J. 70: 1796–1802). Therefore, chemical modification of and site-specific immobilization on mica would extend its field of applications towards more sophisticated molecular architectures.

The complex multilayered structure of mica with its surface-exposed negatively charged honeycomb arrangements of $Si(Al)O_4$ tetrahedra has been used as substrate for monolayer formation of amphiphilic organic molecules, such as alkylphosphonic acids [Woodward et al. (1996) J. Am. Chem. Soc. 118: 7861–7862) and organosilanes (Schwartz, et al. (1992) Phys. Rev. Lett. 69: 3354–3357, Okusa et al. (1994) Langmuir 10: 3577–3581; Hu et al. (1996) Langmuir 12: 1697–1700; Xiao et al. (1996) Langmuir 12: 235–237; Britt et al. (1996) J. Colloid Interface Sci. 178: 775–784). Unfortunately, the former are not robust under aqueous conditions and the latter are often isotropically rough with monolayer formation characterized by low reproducibility, especially if terminated with a nucleophilic group in the w-position.

As an alternative to the attachment of a two-dimensional siloxane network onto the mica surface, efforts have been made to alter the surface chemistry by exchanging the surface cations (mostly potassium) at the basal (001) cleavage plane with other inorganic and organic ions (Shelden et al. (1993) J. Colloid Interface Sci., 157: 318–327; Hähner et al. (1996) J. Chem. Phys. 104: 7749–7757). Surfactant adsorption of long-chain alkylammonium salts, such as cetyltrimethylammonium bromide (CTAB) (Sharma et al. (1996) *Langmuir* 12: 6506–6512; Eriksson et al. (1996) *J. Colloid Interface Sci.* 181: 476–489) and N-dodecylpyridinium chloride (NDP) (Shelden et al. (1993) *J. Colloid Interface Sci.*, 157: 318–327) are known to hydrophobize negatively charged minerals. Exchange with bivalent cations has been used to mediate binding of DNA for SPM studies (Hansma et al. (1995) *Biophys. J.* 68: 1672–1677). Similarly, 2,2'-azobisisobutyramidine hydrochloride (AIBA) has been used as an azo initiator for the polymerization of styrene directly on the mica surface (Shelden et al. (1993) *J. Colloid Interface Sci.*, 157: 318–327; Shelden et al. (1994) *Polymer*, 35: 1571–1575).

There thus exists a need for a rapid and reproducible one step-process for attaching polypeptides, and other moieties such, to a solid surface. Ideally, such a method should be easy to perform and efficient. In addition, it should preferably result in appropriate presentation of critical epitopes, binding sites, and/or active sites. The present invention satisfies these needs and provides related advantages as well.

SUMMARY OF THE INVENTION

This invention provides methods and materials for the controlled (oriented) attachment of virtually any moiety to an atomically smooth surface. The invention is premised, in part, on the surprising discovery that arginine, more preferably polyarginine molecules show a highly specific interaction with the surfaces of layered silicates mediated, at least in part, by a cation exchange with the silicate surface. Unlike previously described cation exchange systems, binding of the arginine tag is highly resistant to physiologically relevant (compatible) concentrations of sodium and other ions.

In one embodiment, this invention provides methods of attaching a moiety to a layered silicate surface. The methods involve covalently attaching the moiety to an arginine tag and contacting the arginine tag with the layered silicate surface. The arginine tag can comprise at least two argine residues (or arginine residue analogs) and preferably comprises from about two to about 100 arginine residues. The arginine tag can be an arginine homopolymer consisting only of arginine residues or it can be a heteropolymer comprising arginine residues and other moieties (e.g., other amino acids). Where the arginine tag is a heteropolymer, the arginine residues can occur in one or more stretches having at least 2, preferably at least 4, more preferably at least 6, and most preferably at least 10 contiguous arginine residues. One preferred layered silicate is mica (e.g., a muscovite mica). The method can further comprise contacting the layered silicate with a solution containing a sodium salt in a concentration (e.g., 1 mM–200 or even 300 mM $Na^+$) sufficient to remove molecules bound to the layered silicate by non-specific ion exchange. The moiety can be virtually any object, or article of manufacture including, but not limited to biological moieties such as cells, tissues, organelles, and various biomolecules (e.g., proteins, nucleic acids, lipids, glycoproteins, polysaccharides, and the like). Proteins and nucleic acids are particularly preferred moieties. A protein can be chemically conjugated to the arginine tag or fused to the amino or carboxyl terminus of the arginine tag. Where the protein is fused, the protein can be recombinantly expressed as a fusion protein with the arginine tag. Particularly preferred proteins include DNA binding proteins, molecular motors, an actin filament, a microtubule, a myosin filament, an actin binding protein, and a myosin filament binding protein.

In another embodiment, this invention provides a surface functionalized for the attachment of organic molecules where the functionalization is compatible with physiological sodium salt concentrations (e.g., a the concentration of NaCl in human blood). The surface can comprise a layered silicate contacted with any of the arginine tag molecules described herein. The arginine tag can be directly functionalized or covalently joined to a molecule selected from the group consisting of a protein, an antibody, a DNA binding protein, a molecular motor, an actin filament, a microtubule, a myosin filament, an actin filament binding protein, a myosin filament binding protein, a cell surface receptor, a growth factor, a hormone, and a nucleic acid. In one particularly preferred embodiment, the arginine tag is fused to the amino or carboxyl terminus of a polypeptide. The fusion can be chemical created or recombinantly expressed.

In still another embodiment, this invention provides methods of orienting a polypeptide on a layered silicate surface (e.g., a mica surface). The methods involve providing a polypeptide covalently linked to an arginine tag; and contacting the arginine tag with the layered silicate surface. Any of the arginine tags described herein are suitable. The methods can additionally involve contacting the surface with a sodium salt in a concentration sufficient to remove molecules bound to the layered silicate by ion exchange. Suitable polypeptides can include molecular motors, actin filaments, microtubules, myosin filaments actin filament binding proteins, myosin filament binding proteins, and the like.

In yet another embodiment, this invention provides a surface bearing anisotropically oriented proteins. The surface can comprise a mica surface contacted with a plurality of proteins, each protein covalently attached to the surface through an arginine tag. The arginine tag can include any of the arginine tags described herein. Preferred polypeptides include molecular motors, actin filaments, microtubules, myosin filaments, actin filament binding proteins, myosin filament binding proteins, and the like.

This invention also provides methods of purifying a target molecule from a heterogeneous mixture of molecules. The methods involve providing a target molecule attached to an arginine tag and then contacting the target molecule with the surface of a layered silicate whereby the target molecule binds to the layered silicate surface. Again, the arginine tag can include any of the arginine tags described herein. The purification methods can additionally involve contacting the layered silicate surface with a sodium salt and/or with a potassium salt, an argine, or a polyarginine in a concentration sufficient to release the target molecule. The contacting of the mixture with the layered silicate can involve flowing the heterogeneous mixture over one or more layered silicate (e.g., mica surfaces) and/or combining the layered silicate (e.g., mica) the heterogeneous mixture. The methods can also involve removing (e.g., via centrifugation) the layered silicate from the heterogeneous mixture. The methods can also involve contacting the layered silicate with a c a potassium salt, an arginine, or a poly-arginine. In one embodiment, the target molecule is any of the fusion polypeptdides described herein. The layered silicate used in the purification can include a mica powder or a mica flake.

This invention additionally provides affinity purification devices. Preferred devices comprise a vessel such as a chromatography column or any other vessel equipped with an inlet and an outlet port. The vessels contain a bed of layered silicate. The layered silicate can include a powdered layered silicate (e.g., powdered mica) and/or a mica flake. In a preferred embodiment, the ports are compatible with the frit of a syringe.

Definitions

The terms "isolated" "purified" or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "arginine" or "arginine residue" as used herein refers to natural, synthetic, or modified arginine amino acids. An arginine can also include arginine analogs that offer the same or similar functionality as natural arginine with respect to their ability to be incorporated into a polypeptide and to interact with a layered silicate.

The phrase "nucleic acid encoding" or "nucleic acid sequence encoding" refers to a nucleic acid that directs the expression of a specific protein or peptide. The nucleic acid sequences include both the DNA strand sequence that is transcribed into RNA and the RNA sequence that is translated into protein. The nucleic acid sequences include both full-length nucleic acid sequences as well as shorter sequences derived from the full-length sequences. It is understood that a particular nucleic acid sequence includes the degenerate codons of the native sequence or sequences which may be introduced to provide codon preference in a specific host cell. The nucleic acid includes both the sense and antisense strands as either individual single strands or in the duplex form.

The term "immunoassay" is an assay that utilizes an antibody to specifically bind an analyte. The immunoassay is characterized by the use of specific binding properties of a particular antibody to isolate, target, and/or quantify the analyte.

The term "molecular motor" refers to a molecule that utilizes chemical energy to produce mechanical force and drives the motile properties of muscle or the cytoskeleton.

Layered silicates are a group of laminated silica minerals that include, but are not limited to vermiculite, montmorillonite, bentonite, hectorite, fluorohectorite, hydroxyl hectorite, muscovite boron fluorophlogopite, hydroxyl boron phlogopite, and the like.

The term fusion protein refers to a protein (polypeptide) composed of two polypeptides that, while typically unjoined in their native state native state, typically are joined by their respective amino and carboxyl termini through a peptide linkage to form a single continuous polypeptide. It will be appreciated that the two polypeptide components can be directly joined or joined through a peptide linker/spacer.

The phrases "compatible with physiological sodium salt concentrations" or compatible with "salt concentrations" are used herein to indicate that the bond formed between a arginine tag and a layered silicate is substantially stable to physiological sodium salt concentrations or to salt concentrations of a particular strength. The term "substantially stable" us used herein to indicate that at least 50%, preferably at least about 80%, more preferably at least about 90%, and most preferably at least about 95%, 98%, or even 99% of a moiety attached to a layered silicate surface, remains attached to the layered silicate when contacted with the stated salt solution.

The terms "normal physiological conditions" is used herein to refer to conditions that are typical inside a living organism or a cell. While it is recognized that some organs or organisms provide extreme conditions, the intra-organismal and intracellular environment normally varies around pH 7 (i.e. from pH 6.5 to pH 7.5), contains water as the predominant solvent, and exists at a temperature above 0° C. and below 50° C. Similarly, "physiological salt concentrations" refer to the concentrations of a particular salt typically found within an organism. Again, it will be recognized that the concentrations of various salts depends on the organ, organism, cell, or cellular compartment used as a reference. Nevertheless, the concentrations of various salts vary between generally well known limits and average concentrations are represented by the salt concentrations provided in standard ringers solutions. One measure of a physiological concentration of a sodium salt is the concentration of sodium chloride in human blood.

The term "moiety" when referred to in the context of attaching a moiety to a surface is used to refer to essentially any composition or molecule that is to be attached to the surface. The moiety can include macroscopic compositions (e.g., an article of manufacture, a bead, etc.) and microscopic compositions, including for example, a biological molecule (biomolecule), an organelle, a cell, a tissue, virtually any naturally occurring natural or synthetic material that is chemically compatible with arginine tag. In a particularly preferred embodiment, the arg-tag attached moieties are biological molecules including, but not limited to, proteins, carbohydrates, lipids, and nucleic acids. Particularly preferred biological molecules include antibodies, DNA binding proteins, molecular motors, actin filaments, myosin filaments, microtubules, actin filament binding proteins, and the like.

DETAILED DESCRIPTION

Figures 1, 2:
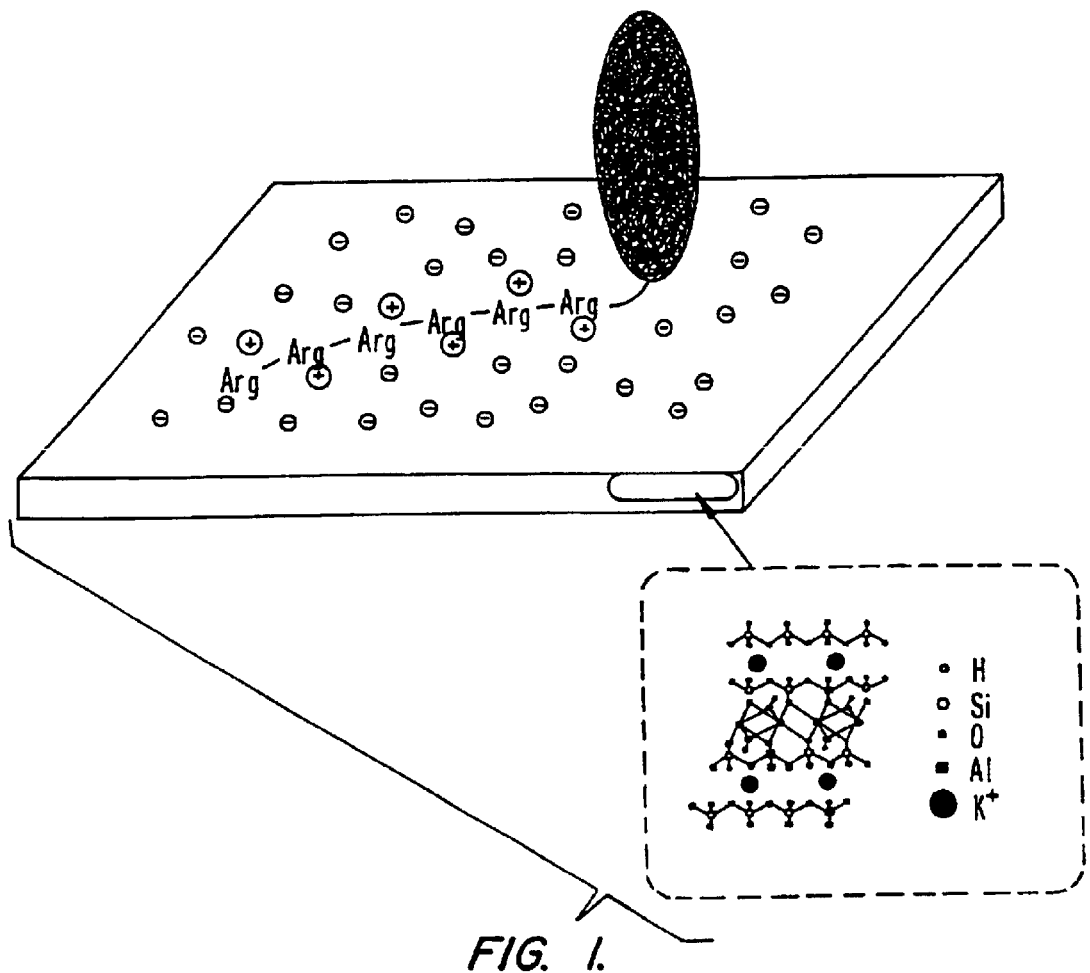
FIG. 1 schematically illustrates a protein immobilized to the mica surface via its Arg-tag (SEQ ID NO:8) (not drawn to scale). The muscovite mica structure is shown in the inset.
FIG. 2 schematically illustrates three different GFP variants. The N- and C-terminally added sequences (SEQ ID NOS:5–7) are shown in the one letter amino acid code. The hexaarginine tag is marked in bold letters and the GFP is shown as a gray bar.

This invention provides novel materials and methods for the attachment of proteins, or other moieties, to solid surfaces, in particular to the surfaces of layered silicates. The methods and materials are particularly advantageous in that the attachment is easily reversed (undone) and yet stable to physiologically relevant concentrations of ions such as $K^+$, $Na^+$, $Mg^{2+}$, $Ca^{2+}$ and the like. In addition, because the precise point of attachment of the protein (or other moiety) can be predetermined, it is possible to prepare proteins bound to surfaces in which critical binding, recognition, or reactive sites are free (or attached) to the surface and thus able to participate in various reactions. Moreover the precise attachment permits the proteins to be uniformly oriented on the surface. The result is that, for a given amount of protein on the surface, a higher number and/or density of reaction sites can be provided than are available using other attachment methods. In addition, because layered silicates (e.g., mica) can be easily fractured to produce atomically smooth surfaces, bound proteins, or other moieties, are not hidden or masked from reactive agents by surface irregularities.

This invention, is premised, in part, on the discovery that an arginine tag (e.g., a single arginine or a series of arginine molecules covalently linked together) will interact with the surface of layered silicates (i.e., negatively charged layered silicates such as mica) and form a highly specific interaction with the layered silicate surface. Without being bound to a particular theory, it is believed that the guanidino group (—NH—C(=NH)—$NH_2$) of the arginine participates in a cation exchange with the layered silicate surface. The reaction, however, appears to be more specific than a simple ion exchange (possibly involving precise steric relationships) and consequently, the adhesion is substantially more resistant to dissociation by various cations such as sodium. Thus, the attachment is stable to physiologically relevant concentrations of cations such as $Mg^{2+}$ (10 mM or greater), $Na^+$ (100 mM or greater), and so forth.

This previously unknown binding reaction between arginine or polyarginine and a layered silicate can be used to reversibly attach virtually any moiety to the layered silicate surface. In another embodiment, the binding reaction can be used to purify (isolate) a protein, or other arg-tag labeled, moiety from a heterologous collection of molecules.

I. Attachment of a Moiety to a Layered Silicate Through an Arginine Tag

The arginine- or polyarginine-tag (referred to herein as an arginine-tag or arg-tag) can be utilized to attach virtually any moiety to the surface of a layered silicate. The attachment method essentially involves attaching the arg-tag to the moiety it is desired to attach to the layered silicate surface and contacting the arg-tag to that surface. Contacting is preferably under conditions (e.g., salt, temperature and pH) in which the arg-tag participates in a binding reaction (e.g., an ion exchange reaction) with the surface whereby the arg-tag becomes bound to the surface.

The arg-tag can be bound to the layered silicate surface first and then reacted with the moiety it is desired to attach to the surface. Alternatively, the arg-tag can be attached to the moiety it is desired to attach to the surface first and then contacted with the layered silicate surface, or the arg-tag can be attached to the moiety and contacted with the surface essentially simultaneously (e.g., in a single reaction).

Binding of the arg-tag to the surface or of the arg-tag and its attached moiety to the surface can essentially functionalize the surface for subsequent reactions. Thus, for example, where just the arg-tag is attached to the surface, the amino acid or polypeptide provides a free amino and a free carboxyl terminus suitable for subsequent reaction (e.g., to attach another molecule). The arginine tag itself can be derivatized with a functional group to attach other molecules and/or, the arg-tag can be used to anchor a second molecule (e.g., a linker) which itself bears one or more reactive sites (e.g., —SH, —$NH_2$, —COOH, —OH, etc.) capable participating in reactions with other molecules. Suitable linkers such as maleimide and others are well known to those of skill in the art.

It will be appreciated that multiple moieties can be attached to a single arg-tag or, conversely, multiple arg-tags can be attached to a single moiety. However, in a preferred embodiment, a single moiety is attached to a single arg-tag.

As indicated above, virtually any moiety can be attached to a layered silicate surface using the methods of this invention. The moiety can include macroscopic compositions (e.g., an article of manufacture, a bead, etc.) and microscopic compositions, including for example, a biological molecule (biomolecule), an organelle, a cell, a tissue, virtually any naturally occurring natural or synthetic material that is chemically compatible with arginine tag. In a particularly preferred embodiment, the arg-tag attached moieties are biological molecules including, but not limited to, proteins, carbohydrates, lipids, and nucleic acids. Particularly preferred biological molecules include antibodies, DNA binding proteins, molecular motors, actin filaments, myosin filaments, microtubules, actin filament binding proteins, microtubule binding proteins, nucleic acids, ribozymes, lectins, enzymes, ligands, receptors, growth factors, cytokines, and the like.

II. The Arginine Tag

A) The Simple Arg-Tag

The arginine tag comprises one or more arginine molecules. In a preferred embodiment, the argine tag comprises at least two arginine molecules, and hence, may be referred to as a polyarginine tag. The length of the arginine tag has no theoretical upper limit and the arginine tag, in principle, can be hundreds, thousands, or even tens of thousands of residues in length. However, it will be appreciated that there are practical and commercial limitations to the tag size. For example, where the arg-tag size interferes with the bound moiety, where the addition of additional residues does not significant improve binding, or where the arg-tag is of a length that renders it difficult to synthesize, express or purify. Thus, in a preferred embodiment, the arg-tag will comprise less than about 1000 arginine residues, preferably less than about 500 arginine residues, more preferably less than about 100 residues, still more preferably less than about 50 arginine residues, and still most preferably less than about 30 or about 20 arginine residues.

Similarly, as shown in Example 1, a single arginine will effectively bind to a layered silicate. However, more arginine residues provide stronger binding. Thus, in a preferred embodiment, the arg-tag comprises at least two arginine residues, more preferably at least about 4 arginine residues, and most preferably at least about 6, 8, 10, or even 15 arginine residues. Thus preferred arg-tags include about 1 to about 100 arginine residues, more preferably about 4 to about 50 arginine residues and most preferably about 6 to about 40 arginine residues.

The arginine residues comprising the arg-tag need not be contiguous. Thus, the arg-tag may contain amino acid residues interspersed between the arginine residues. In this instance, the arginine tag may comprise individual arginine residues separated by one or more other amino acid residues, or alternatively, may comprise stretches of two or more contiguous arginine residues interspersed with one or more other amino acid residues. Alternatively, the arg-tag need not even be a peptide, but rather may consist of arginine or polyarginine residues joined by linker molecules (e.g., straight or branched-chain carbon linkers, or peptide nucleic acids, etc.). However, in a preferred embodiment, particularly where the arg-tag is recombinantly expressed, a polypeptide arg-tag is preferred.

To achieve high density packing of attached moieties on the layered silicate it is often preferred to provide an arg-tag of relatively small size, or one in which the concentration of guanidino groups (number of guanidino groups per Da of argine-tag) is high. In this instance an arginine-tag consisting entirely of arginine residues is preferred. Such an arginine-tag may be referred to as a homoarginine tag.

B) The Modified Arg-Tag

The arginine tags of this invention are not limited to naturally occurring arginine residues. The arginine residues can be chemically modified according to any of a number of means well known to those of skill in the art as long as the guanidino group(s) are maintained in a conformation that permit contact with the silicate surface. Alternatively, the arg-tag can comprise one or more non-amino acid arginine analogues containing guanidio groups. Thus, for example, the arginine can be decarboxylated or the α-amino group can be modified by any of a number of well known reactions (e.g., acetylation). Alternatively, the secondary amine can be substituted (e.g., with methylene or other groups).

C) Location of the Arginine-Tag

Where the arginine tag is attached to a polymer (e.g., a biopolymer such as a polypeptide, or nucleic acid) the arginine tag is attached either at the end of the polymer or at one or more locations within the polymer. Thus, for example, where the polymer is a polypeptide, the arginine tag can be attached to the amino or carboxyl terminal or to the amino or carboxyl terminal amino acids through their respective side chains. Alternatively, where it is desired to leave the polypeptide termini free (e.g., to interact with other molecules) the arginine tag be inserted within the polypeptide. In this instance, the arginine tag is preferably located in an internal domain in which its presence does not interfere with the property of the polypeptide it is desired to exploit.

Thus, for example, where it is desired to a attach a myosin molecule to a surface in a manner that leaves the myosin tails free to interact with other molecules, the myosin molecule may be attached to the silicate surface by an internal rather than a terminal arginine tag. One preferred site for the placement of such an attachment tag in a myosin is in loop 2 which is at the actin binding face of the molecule opposite to the tail (see, e.g., Spudich (1994) *Nature*, 372: 515–518).

The same principles hold true for the attachment of other biological molecules. Thus, for example, the arginine tag can be attached to a terminal or be placed internally in nucleic acids, polysaccharides, glycoproteins, and the like. Again, in a preferred embodiment, the arginine tag(s) are placed in site(s) selected so as to leave domains having the desired activity free from the surface.

It will also be appreciated that an arginine-tag need not be the only tag on the subject moiety. One or more additional tags may be present in addition to the arginine tag(s). The use of multiple tags will permit detection, immobilization, and/or detection under different conditions (e.g., salt, pH, etc.). Virtually any tag and/or label may be additionally be present. Such tags are well known to those of skill in the art. One example of a multiply tagged moiety is a polypeptide tagged both with a polyhistidine and a polyarginine as shown in Example 1.

III. Layered Silicates

The methods of this invention means for the attachment of virtually any moiety to a layered silicate surface. Layered silicates such as mica, are well known to those of skill in the art. These are a group of laminated silica minerals that include, but are not limited to, vermiculite, montmorillonite, bentonite, hectorite, fluorohectorite, hydroxyl hectorite, boron fluorophlogopite, hydroxyl boron phlogopite, and the like. It is also contemplated that negatively charged layered silicate composite materials are also suitable. Silicate composite materials include least one mica and a structurally compatible species. Methods of preparing silicate composites are well known to those of skill in the art (see, e.g., U.S. Pat. Nos. 4,239,519, 4,297,139, and 4,339,540).

Particularly preferred micas are those that can be fractured to produce a smooth surface, more preferably an atomically smooth surface. Due to its extreme flatness (smoothness at an atomic scale) and hydrophilic surface, mica has been established as a standard substrate for electron and scanning probe microscopy applications (see e.g., Zahn et al. (1993) *J. Mol. Biol.*, 229: 579–584; Yang et al. (1994) *FEBS Lett*. 338: 89–92; Guckenberger et al. (1994) *Science* 266: 1538–1540; Mueller et al. (1996) *Biophys. J.* 70: 1796–1802). In a most preferred embodiment, the layered silicates are micas with the structure $KAl_2[AlSi_3O_{10}](OH,F)_2$, which include a group of layered aluminosilicate minerals whose crystals exhibit a large degree of basal cleavage, allowing them to be split into very thin atomically flat sheets.

IV. Covalent Attachment to an Arg-Tag

The moiety it is desired to attach to a layered silicate surface via an arginine-tag, can be covalently attached to the arginine tag according to any of a variety of methods well known to those of skill in the art. In one approach, the arginine tag can be recombinantly expressed or chemically synthesized and then chemically conjugated to the moiety. Alternatively, particularly where the moiety is a polypeptide, a nucleic acid or a peptide nucleic acid, the arg-tag can be synthesized as a part of the process of chemically synthesizing the polypeptide, nucleic acid or peptide nucleic acid. Where the moiety is a polypeptide, the arg-tag can be recombinantly expressed as a fusion protein with the polypeptide moiety.

A) Chemical Conjugation

In one embodiment, the arg-tag is chemically conjugated to the moiety (e.g., polypeptide) it is desired to attach to the layered silicate surface. Means of chemically conjugating molecules are well known to those of skill in the art.

The procedure for a moiety to an arg-tag molecule will vary according to the chemical structure of the moiety. Polypeptides typically contain variety of functional groups; e.g., carboxylic acid (COOH) or free amine ($-NH_2$) groups, which are available for reaction with a suitable functional group on the arg-tag or on a linker attached to the arg tag to bind the polypeptide thereto.

Alternatively, the arg-tag and/or moiety may be derivatized to expose or attach additional reactive functional groups. The derivatization may involve attachment of any of a number of linker molecules such as those available from Pierce Chemical Company, Rockford, Ill.

A "linker", as used herein, is a molecule that is used to join the arg-tag to the moiety. A preferred linker is capable of forming covalent bonds to both the arg-tag and to the moiety molecule. Suitable linkers are well known to those of skill in the art and include, but are not limited to, straight or branched-chain carbon linkers, heterocyclic carbon linkers, or peptide linkers. Where the arg-tag and the moiety that is to be attached to the silicate surface are both polypeptides, the linkers may be joined to the constituent amino acids through the amino acid side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a an arg-tag, and another group reactive with a group on the moiety that is to be attached may be used to form the desired arg-tag conjugate. Alternatively, derivatization may involve chemical treatment of the arg-tag and/or the moiety that is to be attached. For example, where a glycoprotein (e.g., an antibody) is to be attached to the arg tag, glycol cleavage of the sugar moiety of a the glycoprotein using periodate will generate free aldehyde groups. The free aldehyde groups glycoprotein may be reacted with free amine or hydrazine groups on an arg-tag to bind the agent thereto (see, e.g., U.S. Pat. No. 4,671,958). Procedures for generation of free sulfhydryl groups on polypeptides, such as antibodies or antibody fragments, are also known (see, e.g., U.S. Pat. No. 4,659,839).

Many procedures and linker molecules for attachment of various compounds including radionuclide metal chelates, toxins and drugs to proteins such as antibodies are known and can be easily modified for attachment to an arginine tag (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071–4075). In particular, the linkages involved in the production of immunotoxins are particularly well suited for attachment of various moieties to the arginine tags. Such immunotoxin production methods are well-known within the art and can be found, for example in Thorpe et al., *Monoclonal Antibodies in Clinical Medicine*, Academic Press, pp. 168–190 (1982), Waldmann (1991) *Science*, 252: 1657, U.S. Pat. Nos. 4,545,985 and 4,894,443.

In some circumstances, it is desirable to free the argine tag from the attached moiety. Therefore, conjugates comprising linkages which are cleavable in the vicinity of the target site may be used when the arginine-tag is to be released at the target site. Cleaving may be accomplished by enzymatic activity or particular chemical conditions.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at a tumor the target site in vivo by the proteolytic enzymes of the patient s complement system. In view of the large number of methods that have been reported for attaching a variety of radiodiagnostic compounds, radiotherapeutic compounds, drugs, toxins, and other agents to antibodies one skilled in the art will be able to determine a suitable method for attaching an arginine-tag to virtually any moiety.

B) Chemical Synthesis of Arginine-Tagged Fusion Proteins

Where the moiety that is to be attached to the silicate surface is a polypeptide, nucleic acid, or peptide nucleic acid, the arg-tag labeled molecule can be chemically synthesized de novo. For example, where the moiety is a polypeptide and the arg-tag and moiety are relatively short (i.e., less than about 50 amino acids) they may be synthesized using standard chemical peptide synthesis techniques. Where both molecules are relatively short the chimeric molecule may be synthesized as a single contiguous polypeptide. Alternatively the arg-tag and the polypeptide moiety may be synthesized separately and then fused by condensation of the amino terminus of one molecule with the carboxyl terminus of the other molecule thereby forming a peptide bond. Alternatively, the arg-tag and polypeptide moiety may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology*. Vol. 2: *Special Methods in Peptide Synthesis, Part A.*, Merrifield, et al. *J. Am. Chem. Soc.*, 85: 2149–2156 (1963), and Stewart et al., *Solid Phase Peptide Synthesis*, 2nd ed. Pierce Chem. Co., Rockford, Ill. (1984).

Similarly, where the moiety to be attached to the silicate surface is a peptide nucleic acid. The peptide nucleic acid can be synthesized first and the free terminus used as an initiation point for arginine-tag synthesis, or conversely, the arginine tag can be synthesized first and the free terminus used as an initiation point for peptide nucleic acid synthesis. As used herein a peptide nucleic acid refers to nucleotides attached to each other through a peptide backbone. Methods of synthesizing peptide nucleic acids can be found in U.S. Pat. Nos. 5,539,083 and 5,539,082.

Where the moiety to be attached to the silicate is a nucleic acid, the arginine-tagged nucleic acid can also be synthesized de novo. Methods of nucleic acid synthesis include, but are not limited to the phosphoramidite method described by Beaucage and Carruthers (1981) *Tetrahedron Lett.* 22:1859–1862, or the triester method according to Matteucci et al. (1981) *J. Am. Chem. Soc.*, 103:3185. Synthesis of the arg-tag labeled nucleic acid involves either first synthesizing the arg-tag and then utilizing the free terminus of the arg tag as an initiation point for oligonucleotide synthesis, or conversely, first synthesizing the oligonucleotide and then using the free oligonucleotide as an initiation point for peptide synthesis. Compatible oligonucleotide/peptide chemistries are well known to those of ordinary skill in the art C) Recombinant Expression of Polyarginine-Tagged Fusion Proteins In a particularly preferred embodiment, the arginine tagged fusion proteins of the present invention are synthesized using recombinant DNA methodology. Generally this involves creating a DNA sequence that encodes the an arginine tag fused to either the amino or carboxyl terminus of a polypeptide it is desired to attach to the silicate surface. The fusion can be direct or can involve a peptide linker that provides spacing between the arginine tag and the polypeptide or that adjusts reading frame, etc. The nucleic acid encoding the fusion protein is placed in an expression cassette under the control of a particular promoter, a host cell is transfected with the expression cassette, the fusion protein is expressed in the host cell, isolated, and if required, renatured.

The arginine-tag fusion protein expression cassettes can be constructed according to ordinary methods well known to those of skill in the art. Construction of these cassettes is exemplified in Example 1.

The constructs can all be created using standard amplification and cloning methodologies well known to those of skill in the art. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif.; Sambrook et al. (1989) *Molecular Cloning, A Laboratory Manual* (2nd ed.) Vol. 1–3, Cold Spring Harbor Laboratory, Cold Spring Harbor Press, NY; *Current Protocols in Molecular Biology*, F. M. Ausubel et al., eds., Current Protocols, a joint venture between Greene Publishing Associates, Inc. and John Wiley & Sons, Inc., (1994 Supplement); Cashion et al., U.S. Pat. No. 5,017,478; and Carr, European Patent No. 0,246,864.

Examples of techniques sufficient to direct persons of skill through in vitro amplification methods are found in Berger, Sambrook, and Ausubel, supra., as well as Mullis et al., U.S. Pat. No. 4,683,202; Innis et al. (1990) PCR Protocols A Guide to Methods and Applications, Academic Press Inc. San Diego, Calif.; Arnheim & Levinson (Oct. 1, 1990) C&EN, 36–47; Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem.*, 35: 1826; Landegren et al. (1988) *Science*, 241: 1077–1080; Van Brunt (1990) *Biotechnology*, 8: 291–294; Wu and Wallace (1989) *Gene*, 4: 560; and Barringer et al. (1990) Gene, 89: 117.

1) Expression in Prokaryotes

A variety of prokaryotic expression systems may be used to express arg-tag polypeptide fusion proteins. Examples include, but are not limited to, *E. coli*, Bacillus, Streptomyces, and the like.

Prokaryotic expression plasmids preferably contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky (1984) *J. Bacteriol*, 158: 1018–1024 and the leftward promoter of phage lambda (P) as described by Herskowitz, et al. (1980), *Ann. Rev. Genet.*, 14: 399–445. The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

The polypeptides produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration (see, e.g., U.S. Pat. No. 4,511,503).

2) Expression in Eukaryotes

A variety of eukaryotic expression systems such as yeasts, plants, insect cell lines, and mammalian cells are known to those of skill in the art. As explained briefly below, the polyarginine tagged fusion proteins may also be expressed in these eukaryotic systems.

a) Expression in Yeast

Synthesis of heterologous proteins in yeast is well known and described. *Methods in Yeast Genetics*, Sherman et al., Cold Spring Harbor Laboratory, (1982) is a well recognized work describing the various methods available to produce the polypeptides in yeast.

Preferred yeast expression systems are described in Wahleithner et al. (1991) *Proc. Natl. Acad. Sci. USA* 88:10387–10391, Murphy and Lagarias (1997) *Photochem. Photobiol.*, 65: 750–758, and Wu et al. (1996) *Proc. Natl. Acad. Sci., USA*, 93: 8989–8994. Further examples of yeast expression are described below. A number of yeast expression plasmids like YEp6, YEp13, YEp4 can be used as vectors. A gene of interest can be fused to any of the promoters in various yeast vectors. The above-mentioned plasmids have been fully described in the literature (Botstein et al. (1979) *Gene*, 8: 17–24; Broach et al. (1979) *Gene*, 8: 121–133).

The polypeptides can be isolated from yeast by lysing the cells and applying standard protein isolation techniques, or the arginine-tag purification techniques described herein, to the lysates. The monitoring of the purification process can be accomplished by using spectroscopic techniques, or by using Western blot techniques or radioimmunoassays, or other standard immunoassay techniques.

b) Expression in Plants

The arginine-tag fusion polypeptides of this invention can also be expressed in plants or plant tissues. Plant tissue includes differentiated and undifferentiated tissues of plants including, but not limited to, roots, shoots, leaves, pollen, seeds, tumor tissue, such as crown galls, and various forms of aggregations of plant cells in culture, such as embryos and calli. The plant tissue may be in plants, cuttings, or in organ, tissue, or cell culture.

The recombinant DNA molecule encoding the arginine-tag fusion polypeptide under the control of promoter sequences may be introduced into plant tissue by any means known to the art. The technique used for a given plant species or specific type of plant tissue depends on the known successful techniques. The various DNA constructs described above may be introduced into the genome of the desired plant by a variety of conventional techniques. For example, the DNA construct may be introduced directly into the genomic DNA of the plant cell using polyethylene glycol precipitation (Paszkowski et al. (1984) *Embo J.* 3: 2717–2722) electroporation and microinjection of plant cell protoplasts (Fromm et al. (1985) *Proc. Natl. Acad. Sci. USA* 82: 5824), or the DNA constructs can be introduced into plant tissue using ballistic methods, such as DNA particle bombardment (Klein et al. (1987) *Nature* 327: 70–73). Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker gene(s) (if present) into the plant cell DNA when the cell is infected by the bacteria. For a review of gene transfer methods for plant and cell cultures see, Fisk et al. (1993) *Scientia Horticulturae* 55: 5–36 (1993) and Potrykus (1990) *CIBA Found. Symp.* 154: 198.

*Agrobacterium tumefaciens*-mediated transformation techniques are the most commonly used techniques for transferring genes into plants. These techniques are well described in the scientific literature. See, for example Horsch et al. (1984) *Science* 233: 496–498, Fraley et al. (1983) *Proc. Natl. Acad. Sci. USA* 80: 4803, and Hooykaas (1989) *Plant Mol. Biol.* 13: 327–336, Bechtold et al. (1993). *Comptes Rendus De L Academie Des Sciences Serie Iii-Sciences De La Vie-Life Sciences* 316: 1194–1199, Valvekens et al. (1988) *Proc. Natl. Acad. Sci. USA* 85: 5536–5540; de la Pena et al. (1987) *Nature* 325: 274–276; Rhodes et al. (1988) *Science* 240: 204–207; Shimamato et al., (1989) *Nature* 338: 274–276); Shuerman et al. (1993) *Scientia Horticulturae* 55: 101–124; James et al. (1989) *Plant Cell Rep.* 7: 658–661, and the like.

Transformed plant cells (e.g., protoplasts) which are derived by any of the above transformation techniques can be cultured to regenerate a whole plant which possesses the transformed genotype and thus expresses the desired fusion protein. Such regeneration techniques rely on manipulation of certain phytohormones in a tissue culture growth medium. Plant regeneration from cultured protoplasts is described in Evans et al. (1983) pp. 124–176 In: *Protoplasts Isolation and Culture, Handbook of Plant Cell Culture*, MacMillan Publishing Company, New York; and *Binding, Regeneration of Plants, Plant Protoplasts*, pp. 21–73; CRC Press, Boca Raton, 1985. Regeneration can also be obtained from plant callus, explants, organs, or parts thereof. Such regeneration techniques are described generally in Klee et al. (1987) *Ann. Rev. of Plant Phys.* 38: 467–486.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

c) Expression in Mammalian and Insect Cell Cultures

Illustrative of cell cultures useful for the production of the arginine-tag fusion polypeptides of this invention are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, Cos-7 or MDCK cell lines.

When the host cell is of insect or mammalian origin illustrative expression control sequences are obtained from the SV40 promoter (Science, 222:524–527, 1983), the CMV I.E. Promoter (*Proc. Natl. Acad. Sci.* 81:659–663, 1984) or the metallothionein promoter (*Nature* 296:39–42, 1982). The cloning vector containing the expression control sequences is cleaved using restriction enzymes and adjusted in size as necessary or desirable and ligated with DNA coding for the arg-tag polypeptides by means well known in the art.

Numerous eukaryotic expression systems (e.g., rotavirus vectors, baculovirus vectors, etc.) are commercially available.

V. Binding of the Arginine-Tagged Moiety to the Silicate Surface

Binding of the arginine-tagged moiety to a silicate surface is accomplished simply by contacting the arginine tagged moiety with the surface. This is preferably accomplished in solution where a solution (preferably an aqueous solution) contains the arg-tag labeled moiety (e.g., arg-tag labeled polypeptide). After the arg-tag labeled moiety is bound to the surface, the solution may optionally be removed and the surface dried.

It is recognized that moieties may contain charge sites (in addition to the arginine-tag) that interact with the silicate surface. In a preferred embodiment, it may be desirable to optimize ionic strength of the solution (e.g., assay solution) surrounding the arg-tag bound moiety to maximize activity of the bound moiety, reduce interaction of the bound moiety with the surface, or minimize other non-specifically bound charged species. This is routinely accomplished by systematically increasing the salt (e.g., NaCl) concentration of the solution until the bound moiety exhibits the desired performance characteristics. Such a systematic adjustment in salt concentration is illustrated in Example 1.

VI. Release of Binding Agents

It is an advantageous feature of this invention that moieties bound to a silicate surface through an arginine-tag are reversibly bound; that is, they may subsequently be released with relative ease. Release can be routinely accomplished simply by competition of the surface bound arg-tag labeled moiety with another material capable of ion exchange with the silicate surface. The concentration of the competing material is simply increased until adequate release is accomplished.

Release can be accomplished with high enough concentrations of virtually any cation, however, as shown in Example 1, release is particularly effective using either $K^+$ or arginine. The cation concentration suitable to effect release of the bound arg-tagged moiety will vary depending on the size of the arginine-tag and the nature of the bound moiety. The concentration however can be determined simply by increasing the cation concentration until adequate release is accomplished. Potassium concentrations in excess of 0.2M and arginine concentrations in excess of 0.1 molar will generally effect adequate release of an arginine-tagged moiety from a layered silicate surface.

From the information provided in Example 1, it will be appreciated that materials showing non-specific binding can be released from the layered silicate surface without effecting release of the arginine-tagged moiety. This is simply accomplished by contacting the surface with a cation in a concentration sufficient to release the non-specifically bound material without releasing substantial quantities of the arginine-tagged material. It was demonstrated in Example 1, that ionic species such as $Na^+$ were highly effective in removing non-specifically bound materials, but significantly less effective in releasing the arginine-tagged moiety. Thus, in a preferred embodiment, differential release of non-specifically bound materials is accomplished by using ionic species such as $Na^+$ or $Mg^{2+}$ rather than potassium. The optimal ion concentration can be determined empirically by increasing the ionic concentration until acceptable removal of undesired material is accomplished without unacceptable removal of the arginine-tagged moiety. In a preferred embodiment, suitable $Na^+$ concentrations will range from about 1 mM to about 200 or even 300 mM.

VII. Use of Arginine-Tagged Proteins in Assays

The materials and methods of this invention are particularly useful for immobilizing biological molecules, including, but not limited to, proteins, antibodies, polysaccharides, lipids, nucleic acids (DNA and RNA), for use in any of a number of assays. Such assays include, but are not limited to molecular motor assays, immunoassays, nucleic acid binding assays.

A) High-Throughput Assays

Because layered silicates provide atomically smooth surfaces, biological molecule attached thereto are fully exposed to applied reagents and not masked within surface irregularities. In addition, the specific nature of the arginine-tag site permits the attachment of molecules in a uniform orientation and allows reactive (e.g., binding) sites to be positioned in a manner that optimizes their interaction with applied reagents (e.g., the reactive site can be positioned away from the substrate). Consequently assays performed with the arginine-tagged moieties on a layered silicate surface are expected to provide higher sensitivity and specificity and therefore a higher signal to noise ratio. Consequently assays can be run more rapidly and/or more reliably. The arginine-tagged moieties on atomically smooth silicate surfaces (e.g., layered silicates) are therefore particularly well suited for high throughput assays.

Conventionally, new chemical entities with useful properties (e.g., inhibition of myosin tail interactions) are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

1) Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487–493, Houghton et al. (1991) *Nature*, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see. e.g., Strategene, Corp.), peptide nucleic acid libraries (see, e.g., U.S. Pat. No. 5,539,083) antibody libraries (see, e.g., Vaughn et al. (1996) *Nature Biotechnology*, 14(3): 309–314), and PCT/US96/10287), carbohydrate libraries (see, e.g., Liang et al. (1996) *Science*, 274: 1520–1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549, 974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville, Ky., Symphony, Rainin, Woburn, Mass., 433 A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

2) High Throughput Assays of Chemical Libraries

Any of the assays for compounds inhibiting the virulence described herein are amenable to high throughput screening. As described above, having identified the nucleic acid associated with virulence, likely drug candidates either inhibit expression of the gene product, or inhibit the activity of the expressed protein. Preferred assays thus detect inhibition of transcription (i.e., inhibition of mRNA production) by the test compound(s), inhibition of protein expression by the test compound(s), or binding to the gene (e.g., gDNA, or cDNA) or gene product (e.g., MnRNA or expressed protein) by the test compound(s). Alternatively, the assay can detect inhibition of the characteristic activity of the gene product or inhibition of or binding to a receptor or other transduction molecule that interacts with the gene product. High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

B) Assay Types

1) Molecular Motor Assays

The materials and methods of this invention are particularly well suited for binding polypeptides to layered silicate solid supports for use in assays related to protein—protein interactions and/or protein-nucleic acid interactions. The methods of this invention are well suited for investigation of protein—protein interactions that underlie the structure and function of molecular motors. In particular the methods of this invention facilitate the creation and execution of assays that screen for compounds that inhibit or enhance interactions (e.g., binding) between cytoskeletal protein components. In a preferred embodiment, the methods involve immobilizing a first cytoskeletal component on a surface (preferably a layered silicate surface) and detecting the presence, absence, affinity and/or specificity of binding of a second component to the first component in the presence and/or absence of a test compound. Alternatively, particularly where the assay involves a "molecular motor" the assay can involve immobilizing, according to the methods of this invention, either the molecular motor or the "track" upon which the motor runs and detecting the respective movement of the non-immobilized component (motor or track). Molecular motor activity assays are well known to those of skill in the art (see, e.g., Gittes et al. (1996) *Biophys. J.* 1: 418–429 and Shirakawa et al. 1995) *J. Exp. Biol.*, 198: 1809–1815).

The number and identify of cytoskeletal components that have been identified thus far are legion, and far too numerous to be completely listed here. A partial listing can be found in the following references: Vale and Kreis (1993) *Guidebook to the Cytoskeletal and Motor Proteins*, New York, Oxford University Press; Goldstein (1993) *Ann Rev. Genetics*, 27: 3109–351; Mooseker and Cheny (1995) *Annu. Rev. Cell Biol.*, 11: 633: 675).

It will be appreciated that the assays of this invention typically involve the interaction of two or more components. Assays involving interactions between two components can be viewed as assays for enhancers or inhibitors of binding between members of "binding pairs". Preferred binding parirs include α-actinen/actin, tropomyosin/actin, vinculin/ actin, villin/actin, kesin/microtubule, dynein/microtubule, myosin/actin, myosin tail/myosin tail, and the like. It will be appreciated that either member of the binding pair can be immobilized (attached to the surface) while the other member is in a solution contacted to the surface. Alternatively, both members can be attached surfaces which are then juxtaposed to perform the assay.

Detailed assays for inhibitors or enhancers of interactions between molecular motor components or cytoskeletal components generally are described in copending application U.S. Ser. No. 60/057,895 entitled "High Throughput Assays for Detecting Modulators of Cyotskeletal Function" filed on Sep. 4, 1997, naming James Spudich, Ron Vale, and Daniel Pierce as inventors.

2) Immunoassays

In conducting immunological tests, one skilled in the art is confronted with the prospect of attempting to discern whether or not a reaction has taken place between related immunological agents (e.g. antigen and antibody). Thus, for example, when it is sought to determine whether and how much of a particular antigen or antibody resides in a body fluid one must attempt to react the fluid suspected of containing this material with its immunological partner. If a reaction takes place, then the visualization of that reaction is evidence of the presence of the antigen or antibody in the originally tested fluid. It is, of course, known that antigens will induce the formation of antibodies in most animals. The relationship between the induced antibody and the antigen is such that when combined in the proper quantities these two materials will form a complex. One of the major problems in the diagnostic field, relative to immunological testing is that this reaction is not very often manifested in a visual event. Thus, the complex may form but might be invisible to the naked eye or may be soluble in the reaction medium.

To overcome this lack of means to characterize the reaction, the art has long employed the technique of utilizing indicator or carrier particles or surfaces upon which is carried the appropriate immunological material. The types of particles used are extremely varied, ranging from biological materials such as red blood cells and tissue culture cells to immunologically inert polymeric particles.

By far the most suitable system has been the polymeric particle technique in which synthetic resin particles, surfaces, or matrices have been used as an adsorbant onto which the appropriate antigen or antibody has been adsorbed. While the latex particle system has been quite suitable and has been employed widely, nevertheless, there are certain characteristics of the system which are undesirable from the point of view of reactant specificity. For some reason, not quite understood fully, while one could have a very specific antibody adsorbed onto an immunologically inert polymeric carrier, it is possible, and quite often the case that the reaction with the fluid containing suspect antigen does not result in easily visualized agglutination products evidencing that reaction. It is thought that at least a partial reason for this is that adsorption onto the particle is too weak a bonding mechanism to enable complete utilization of the particles. That is, some of the adsorbed protein would tend to be desorbed from the particle and while still reactive of course with its immuno partner would then not have its carrier particles attached to it. To the extent that such material is loosened from its particles the agglutination pattern is rendered less discernible.

An increase in binding specificity and/or affinity would mitigate these difficulties. As explained above, because layered silicates provide atomically smooth surfaces, biological molecule attached thereto are fully exposed to applied reagents and not masked within surface irregularities. In addition, the specific nature of the arginine-tag site permits the attachment of molecules in a uniform orientation and allows reactive (e.g., binding) sites to be positioned in a manner that optimizes their interaction with applied reagents (e.g., the reactive site can be positioned away from the substrate). Consequently immunoassays performed with the arginine-tagged moieties on a layered silicate surface are expected to provide higher sensitivity and specificity and therefore a higher signal to noise ratio.

It will be appreciated that whether an antigen or an antibody is attached to the surface through an arginine-tag depends on the assay format. Formats for immunoassays include, but are not limited to competitive (e.g., ELISA, hapten inhibition, etc.) and noncompetitive assays. Various immunoassay formats are well known to those of skill in the art (see, e.g., U.S. Pat. Nos. 4,366,241; 4,376,110; 4,517, 288; and 4,837,168; Asai (1993) *Methods in Cell Biology Volume 37: Antibodies in Cell Biology*, Academic Press, Inc. New York, Stites & Terr, eds. (1991) *Basic and Clinical Immunology* 7th Edition, etc.) and the references cited therein).

3) Nucleic Acid Binding Assays

In another embodiment, the materials and methods of this invention are used to immobilize components in nucleic acid binding protein assays. Typically such assays detect binding of a nucleic acid by one or more binding proteins. The assays are generally used to screen for agents that improve (specificity or affinity) or inhibit nucleic acid binding by one or more particular nucleic acid binding proteins. Nucleic acid binding proteins include, but are not limited to endonucleases, polymerases, nuclear transcription factor receptors, API proteins (e.g., fos and jun).

The assays are facilitated by attachment to a surface of either the nucleic acid containing the protein binding site or the binding protein itself. As explained above, attachment of either of these moieties to an atomically flat (e.g. layered silicate) surface through an arginine tag of this invention is expected to improve sensitivity, selectivity and hence the signal to noise ratio of such an assay. Formats for nucleic acid/binding protein assays are well known to those of skill in the art.

4) Assays in Physiologically Compatible Solutions

It will be appreciated that may of the foregoing assays require particular conditions for the subject assay components (e.g., enzymes) to maintain their desired activity. Typically such assays are optimized to maintain physiologically compatible conditions for elements (e.g., pH, ion composition) critical to component activity.

It is a significant advantage that the arginine tag attachments of this invention are stable to physiological concentrations of most ionic species (e.g., $Na^+$, $Ca^{2+}$, $Mg^{2+}$, etc.) Thus, the assays can be run in standard physiologically compatible compositions (e.g., phosphate buffered saline (PBS) standard ringers solutions, and the like.).

The arginine tags of this invention can also be used to purify the moiety (e.g., polypeptide(s)) to which they are linked. Specifically, the arginine tag can be used in conjunction with virtually any anion or cation exchange resin. (It will be appreciated that an anion resin will be used to capture other species and exclude the arg-tagged moieties.) Because the arginine tags are more charged than other tags in current use, the arginine tags are expected to provide greater affinity to cation resins resulting in more effective purification. Suitable anion and cation exchange resins are well known to those of skill in the art and are commercially available. Cation exchange resins, for example include, but are not limited to, carboxymethylcellulose, while anion exchange resins include, but are not limited to, DEAE cellulose, DEAE SEPHAROSE gel filtration ion exchange media, heparin, and the like.

In one preferred embodiment, the interaction of an arginine tag with a layered silicate can be exploited for purification purposes. This accomplished in a manner analogous to a cation exchange resin or in a manner analogous to the polyhistidine/nickel separation systems substituting mica for the cation exchange resin or the nickel resin, respectively. In one embodiment, the mica is provided as a bed (either of mica flakes or powder) through which the sample is flowed. The mica bed is housed in any of a variety of suitable vessels, including cartridges that are attachable to syringes, chromatography columns, and the like. The arginine tag labeled moiety (e.g. recombinantly expressed arginine tag labeled fusion protein) binds to the mica bed, while other components of the sample are washed away. Non-specifically binding components can be eluted away using salt solutions at concentrations sufficient to release undesired components while retaining the arginine-tagged moiety. The arginine-tagged moiety can then be released by application of sufficient salt concentrations and/or arginine as described above.

In another embodiment, the layered silicate can be added to a vessel containing a sample (e.g. cell lysate) from which the arginine-tagged moiety it to be isolated under conditions in which the arginine tag binds to the silicate. The silicate can then be separated from the sample (e.g., by centrifugation) and the arginine-tagged moiety is then optionally separated from the silicate.

It will be appreciated that where it is desired to subsequently release the arginine tag from the attached moiety the arginine tag can be attached to the moiety via a cleavable linker as described above. Alternatively, where the arginine tag is expressed as a fusion protein with a polypeptide, a cleavage site can be provided between the arginine tag and the polypeptide. Such cleavable linkages are well known to those of skill in the art (see, e.g., U.S. Pat. No. 5,532,142).

It is noted that Example 1 describes a system in which proteins contain either a hexa-histidine or both a hexa-histidine and an arginine tag. The hexa-histidine tagged protein was eluted from an $Ni^{2+}$/NTA matrix using 500 mM inidazole, while 500 mM NaCl was required for the dual-tagged proteins due to the strong arginine-tag interaction with the $Ni^{2+}$/NTA matrix. This indicates that the arginine tag can be used to separate proteins.

IX Use of Arginine-Tags on Atomically Flat Surfaces

It will be appreciated that the atomically flat nature of appropriately fractured layered silicates combined with the regular orientation offered by the arginine tag attachment methods of this invention are highly advantageous in numerous other contexts. For example, increasingly electron microscopy and atomic force microscopy are being used to investigate the structure of biomolecules (e.g., protein). Both techniques are improved by smooth support surfaces, however smooth surfaces are particularly beneficial to atomic force microscopy measurements so that the molecule being measured and the measurement itself display minimal surface variation-induced artifacts.

Similarly, protein structure can be investigated by making 2-dimensional crystals and then using electron microscopes or atomic force microscopes to probe the crystal structure at atomic resolution. Again this requires the use of atomically smooth surfaces to minimize surface induced artifacts. In addition, a regular repeating "crystal" pattern is required which can be provided by the regular attachment of the molecule via an arginine tag.

Control of the orientation of individual molecules attached to a surface via the arginine tags of this invention permits the creation of lithography masks having resolution at an atomic scale. Precise attachment of masking proteins allows the precision etching of microcircuits, nanomachines, and the like.

It will also be appreciated that the attachment methods can be used to make arrays of moieties (e.g., biomolecules). The arrays can include one or more different biomolecules (either the same or different type, e.g., all protein arrays, or mixed protein/nucleic acid arrays) where the spatial location of each species of array element is known. It will be appreciated that using the precise attachment methods of this invention, the moieties can be arranged in extremely precise patterns (e.g., rows of dots, rows of squares, lines, etc.) on a surface.

IX. Kits for the Attachment of Moieties to Arginine Tags

This invention also provides kits for practice of the methods of this invention. In one embodiment, the kits include materials for chemical conjugation of an arginine tag to a moiety. In another embodiment, the kits include materials for the recombinant expression of a polypeptide fused to an arginine tag. The kits can also include materials for the immobilization, isolation and/or purification of an arginine-tagged moiety.

A) Kits for Chemical Conjugation of Arg-Tags

In one embodiment, the kits include materials for chemical conjugation of an arginine tag to a moiety. In particular, the kits include one or more containers containing linkers and/or reagents for the chemical conjugation of an arginine tag to an appropriately functionalized moiety (e.g., a polypeptide, an antibody, etc.) as described above. The kit can optionally include an arginine tag either bound to a linker or functionalized for binding to a linker or direct conjugation to a suitable moiety. The kits may optionally contain any of the buffers, reagents, and/or media that are useful for the practice of the methods of this invention.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

B) Kits for Recombinant Expression and/or Isolation of Arg-Tag Fusion Proteins

In another embodiment, the kits include materials for the recombinant expression of a polypeptide fused to an arginine tag. In particular, the kit can include one or more vectors designed for the production of polypeptide fused to a polyarginine tag. Specifically the vectors will contain restriction sites that facilitate the insertion of a nucleic acid encoding a polypeptide. The vectors will also contain sequences for the expression of an arginine tag of this invention. The vectors may also encode a cleavage site between the polypeptide and the arginine tag. Such vectors are well known for the expression of histidine tagged fusion proteins (see, e.g., the pRSETA His-tag expression plasmid (Invitrogen)). The arginine tag vectors of this invention are preferably analogous substituting the arginine tag coding sequences for the polyhistidine coding sequences.

Again, the kits can optional include any of the instructional materials, buffers, reagents, and/or media that are useful for the practice of the methods of this invention. Preferred instructional materials include protocols for the expression and/or purification of the arginine-tagged fusion polypeptides of this invention.

The kits of this invention can also include layered silicate materials or ion exchange resins for the attachment of arginine-tagged moieties. The layered silicate materials are preferably powdered, flaked, or atomically smooth sheets.

EXAMPLES

The following examples are offered to illustrate, but not to limit the present invention.

Example 1

Reversible, Site-Specific Immobilization of Arginine-Tagged Fusion Proteins on Mica Surfaces This example describes the specific binding of polyarginine tagged proteins to atomically flat negatively charged mica surfaces. The polyarginine tags were expressed as fusion proteins. It is shown herein that the arginine (e.g., hexaarginine) tagged proteins bind to mica via the Arg-tag based on ion exchange of naturally occurring potassium cations. Only nonspecific binding was observed with the control protein that is free of the Arg-tag. This novel technology facilitates the uniform and specific orientation of immobilized proteins on a standard substrate used for many surface-related applications.

Materials and Methods

Materials

Muscovite mica was obtained from Provac (Liechtenstein). The plasmid pGFPuv was from Clontech (Palo Alto, Calif.) and the vector pET28a(+) was from Novagen (Madison, Wis.). All other reagents were from Sigma Chemical (St. Louis, Mo.) and of highest available grade. Ultrapure water with a resistance of 18 MOhm was used for all aqueous buffers (purified by passage through a Milli-Q purification system).

Preparation of $GFPH_6$, $GFPH_6R_6$, $GFPR_6$

For the addition of six histidine residues to the N-terminus of GFP, two oligodeoxyribonucleotide primers were designed: one corresponding to the N-terminal part of the GFP gene (5'-GGAATTCCATATGAGTAAAGGAGAAGAACTTTC-3', designated primer #1, SEQ ID No: 1) and a second corresponding to the C-terminal part (5'-GACCGGCGCTCAGTTGGAATTC-3', designated primer #2, SEQ ID No: 2). These oligodeoxyribonucleotides were used for PCR with 20 ng of linearized pGFPuv as template. The amplified fragments, digested with NdeI and BamHI, were ligated with the linearized expression vector pET28a(+). The resulting plasmid pGFPH6 was used for transformation of *E. coli* BL21(DE3). Standard protocols were followed for DNA handling and bacterial transformation (Sambrook et al. (1989) *Molecular cloning: A laboratory manual*, Cold Spring Harbor: Cold Spring Harbor Laboratory Press).

To introduce a tag of six arginine residues on either the N- or C-terminal part of GFP, the same procedure was used with the following oligodeoxyribonucleotides: (primer #2) and 5'-GGAATTCCATATGCGCCGTCGCCGTCGCCGTAT GAGTAAAGGAGAAGAACTTTTC-3' for GFPH6R6, (primer #1) (SEQ ID NO:4) and 5'TTGGAATTCATTAGC-GACGGCGACGGCGACGCGGGTGCCTTTG-TAGAGCT CATCCATG-3' (SEQ ID NO:9) for GFPR6. The PCR and cloning procedure was performed as described above. The resulting plasmids pGFPH6R and pGFPR6 were used to transform *E.coli* BL21(DE3).

Expression and Purification of the Recombinant Proteins

All of the expressed proteins carry a vector-encoded tag of a hexa-histidine sequence for purification by metal chelate affinity chromatography on a $Ni^{2+}$/NTA matrix (Qiagen, Santa Clarita, Calif.). The cells were grown at 37° C. by shaking in LB-medium containing 25 mg/ml Kanamycin. At an $OD_{600}$ of 0.8 the cells were induced with 1 mM IPTG, and 5 h later, they were harvested by centrifugation at 6000×g for 10 min. The cells were lysed by addition of lysozyme at a concentration of 100 mg/ml and 10% (v/v) of 1% TRITON X-100 non-ionic detergent octylphenol ethylene oxide condensate in 50 mM Tris-HCl pH 7.5, 50 mM KCl, 1 mM EDTA. After incubation for 30 min on ice, $MgCL_2$ was added to a final concentration of 40 mM. The liberated DNA was digested by adding 0.2 mg DNaseI per ml lysate. The lysate was incubated for 15 min on ice and then centrifuged at 30,000×g for 40 min. The clear supernatant was dialyzed against buffer containing 10 mM Hepes/

NaOH pH 7.4, 50 mM NaCl, and then applied to a Ni$^{2+}$/NTA column. Weakly bound proteins were eluted with 10 mM imidazole pH 8.0. The His-tagged proteins were eluted with 500 mM imidazole in the case of GFPH6 and with 500 mM imidazole, 500 mM NaCl for all the other variants (the Arg-tag caused a strong ionic interaction with Ni$^{2+}$/NTA matrix). The eluted proteins were dialyzed against buffer containing 10 mM Hepes/NaOH pH 7.4, 50 mM NaCl, 50% glycerol and stored at −20° C. The purity of the recombinant proteins was estimated by SDS-polyacrylamide gel electrophoresis and found to be greater than 95%.

Protein Adsorption to Mica

Mica sheets were cut into pieces of 5×5 cm$^2$ and freshly cleaved immediately before use. Droplets of protein solutions (GFPH6, GFPR6, GFPH6R6) at a concentration of 10 mg/ml were applied onto the previously unexposed, hydrophilic surfaces resulting in aqueous films of approximately 4 cm$^2$ in size. After incubation for 5 min, the mica sheets were washed with 10 ml of water. The central parts, 1 cm$^2$ in size, were then cut out to ensure that no contaminants from the edges could falsify the subsequent analyses. For each data point four surfaces were analyzed and the readings were averaged. These surfaces, stored separately in Eppendorf tubes, were then subjected to consecutive one-min washing steps with 400 ml 10 mM Hepes/NaOH buffer pH 7.4 containing increasing concentrations of salt with different mono- and bivalent cations (50, 125, 250 mM, Na$^+$, K$^+$, Mg$^{2+}$). For quantitation of active, adsorbed GFP, the eluates were collected separately and analyzed by fluorescence measurement at 509 nm (excitation at 395 nm) using an SLM8000 spectrophotometer (Aminco, Silver Spring, Md.) and GFP of known concentration as standard.

Mica sheets were cut into pieces of 5×5 cm$^2$ and freshly cleaved immediately before use. Droplets of protein solutions (GFPH6, GFPR6, GFPH6R6) at a concentration of 10 mg/ml were applied onto the previously unexposed, hydrophilic surfaces resulting in aqueous films of approximately 4 cm$^2$ in size. After incubation for 5 min, the mica sheets were washed with 10 ml of water. The central parts, 1 cm$^2$ in size, were then cut out to ensure that no contaminants from the edges could falsify the subsequent analyses. For each data point four surfaces were analyzed and the readings were averaged. These surfaces, stored separately in EPPENDORF microcentrifuge tubes, were then subjected to consecutive one-min washing steps with 400 ml 10 mM Hepes/NaOH buffer pH 7.4 containing increasing concentrations of salt with different mono- and bivalent cations (50, 125, 250 mM, Na$^+$, K$^+$, Mg$^{2+}$). For quantitation of active, adsorbed GFP, the eluates were collected separately and analyzed by fluorescence measurement at 509 (excitation at 395 nm) using an SLM8000 spectrophotometer (Aminco, Silver Spring, Md.) and GFP of known concentration as standard.

Amino Acid Adsorption to Mica

To adsorb the amino acids arginine, lysine and histidine on mica, the sheets were cut and freshly cleaved as described above. Droplets of amino acid solutions at a concentration of 25 mM were applied onto the mica. The incubation times, the elution of the adsorbed amino acids with increasing concentrations of NaCl (1 and 10 mM in water), and the detection of the amount of bound amino acids by XPS were performed as described above.

X-Ray Photoelectron Spectroscopy (XPS)

XPS was carried out on a Surface Science Model 150 XPS spectrometer with an AlKα source (1486 eV), a quartz monochromator, hemispherical analyzer, and a multichannel detector. A nickel grid, directly positioned above the samples, and a charge neutralizer were used to prevent artifacts due to charging effects. The spectra were accumulated at a take-off angle of 35° and an angular acceptance of 30°, with a 250×1000 μm spot size at a pressure of less than 1×10$^{-8}$ Torr. The NIs peaks shown in this study are normalized against Si2s and corrected for the number of scans and the atomic sensitivity factors.

Results and Discussion

The strategy presented here for the site-specific immobilization of proteins is based on the ion exchange capacity of naturally occurring cations on the negatively charged cleavage plane of atomically flat mica.

Positively charged polypeptide tags with high affinity to mica were genetically fused to either the N- or C-terminus of GFP. In order to design this tag, the interaction of positively charged amino acids to the mica surface was investigated in a preliminary experiment by XPS measurement.

Table 1 shows the extent of release of arginine, lysine and histidine from the mica surface and its dependence on the salt concentration in the wash buffer. The emitted photoelectrons of the nitrogen atoms of the adsorbed molecules were used to monitor the residual amount of the amino acids on the mica after consecutive washing with increasing concentrations of salt.

TABLE 1

Extent of release of arginine, lysine, and histidine from a mica surface and its dependence on the salt concentration in the wash buffer.

| | Bound Amino Acid (%) | | |
|---|---|---|---|
| Wash | Arg | Lys | His |
| Water | 100 | 100 | 100 |
| 1 mM NaCl | 78 | 54 | 53 |
| 10 mM NaCl | 58 | 36 | 30 |

Although the ratio of the N1s peak signals to the silicon Si1s peak intensities of the underlying silica structure were determined, no attempt was made to calculate the absolute amounts of adsorbates. However, the extent of desorption of the amino acids could be estimated based on the relative photoelectron counts. In this experiment, the amount of bound amino acids after thorough washing with ultrapure water was set to 100%. After a first rinsing step with 1 mM NaCl, 78% of the adsorbed arginine, but only 54% of lysine and 53% of histidine remained on the surface. Further treatment with a 10 mM NaCl solution decreased the amount of bound amino acids to 58, 36 and 30% for Arg, Lys and His, respectively. These data show that arginine is more tightly associated with the mica than the other positively charged amino acids. The extent of ion exchange on the mica surface is associated to the enthalpy of hydration of the cations that are involved. NaCl was used instead of KCl in the salt buffer, because K$^+$ and the positively charged nitrogens of the bulky amino acid have a lower enthalpy of hydration than Na$^+$. This result led to the decision to add a polyarginine tag to a protein. It is noted that the observed binding via the positively charged arginine is consistent with the previously reported binding of positively charged 2,2'-Azobis-isobutyramidine hydrochloride (Sheldon et al. (1993) *J. Colloid. Interface Sci.*, 157: 318–327; Shelden (1994) *Polymer* 35: 1571–1575.). Because of its intrinsic fluorescence, the green fluorescent protein (GFP) from the jellyfish *Aequorea victoria* was chosen as the model protein in this study. GFP has been expressed in a variety of species including bacteria (Chalfie et al. (1994) *Science*, 263: 802–805). The chromophoric group emits efficiently in the green spectral region if the protein is in its native conformation. This allows the quantitation of the amount of native protein that was released from the surface after consecutive elution steps by measuring fluorescence. FIG. 2 gives an overview of the three different GFP constructs that were designed for this experiment. GFPH6 carries an N-terminal His-tag alone in order to facilitate the purification of the protein by $Ni^{2+}$/NTA affinity chromatography. GFPR6H6 carries in addition a stretch of six arginine residues at the N-terminal region, whereas GFPR6 has the same Arg-tag at the C-terminal region and the His-tag at the N-terminus.

In a first experiment the release from mica of all three prebound FP constructs was tested using consecutive washes with increasing concentrations of NaCl, followed by a final wash with 100 mM Arg. Only about 1 pmol of the Arg-tag free GFPH6 remained bound after extensive washing with 10 mM Hepes/NaOH, pH 7.4. In contrast about 3 pmol of both Arg-tagged species remained bound after this wash. Essentially all of the Arg-tag free GFPH6 was removed from the surface by consecutive washing steps with increasing concentrations of NaCl (see columns in FIG. 3 from left to right). In contrast, only about 50% of the two GFP variants comprising hexaarginine-tags (GFPR6H6 and GFPR6) came off with NaCl. The complete release could be achieved by elution with arginine-containing wash buffer (final column in FIG. 3). It is rather likely that this arginine-releasable protein was exclusively bound via its Arg-tag, whereas that released in the NaCl washing steps stemmed primarily from protein electrostatically bound to the surface via other charged groups in the protein.

Figure 3:
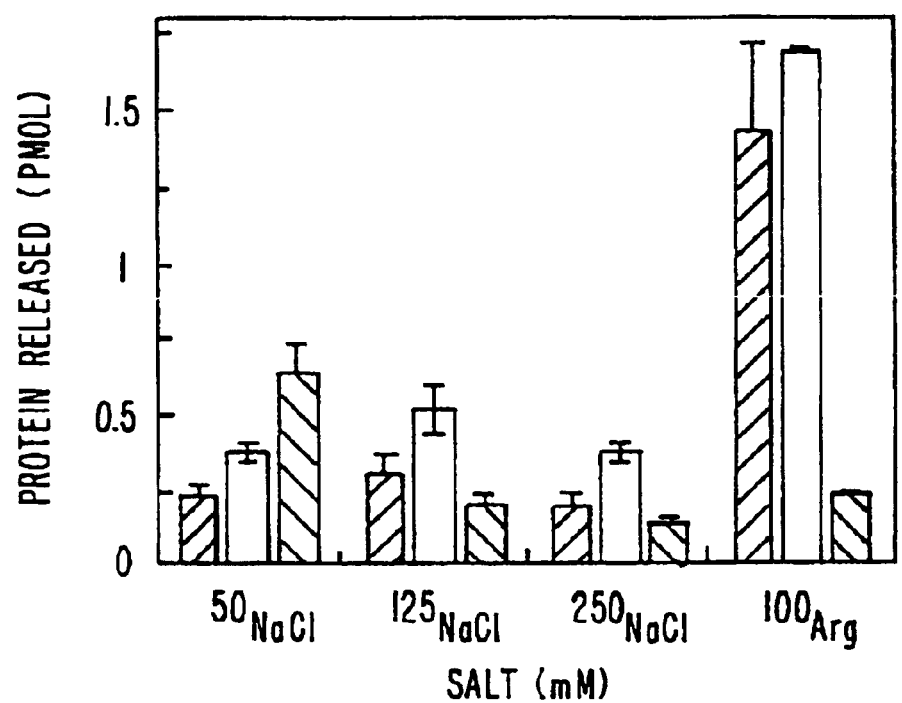
FIG. 3 indicates stepwise elution of immobilized protein as a function of consecutive washes of the same surface with increasing NaCl concentration in the wash buffer followed by a 100 mM Arg wash. The values for $GFPR_6$, $GFPH_6R_6$ and $GFPH_6$ are shown in black, light gray and dark gray, respectively.
Figure 4A:
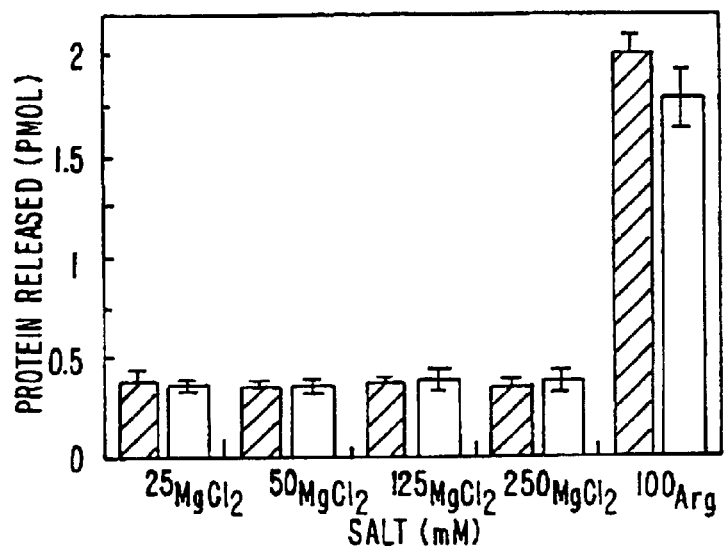
FIG. 4 shows the dependency of the elution of immobilized protein on $MgCl_2$ (A), KCl (B) and Arg (C) concentration. GFPR6 is shown in black and GFPH6R6 is shown in light gray.
Figure 4B:
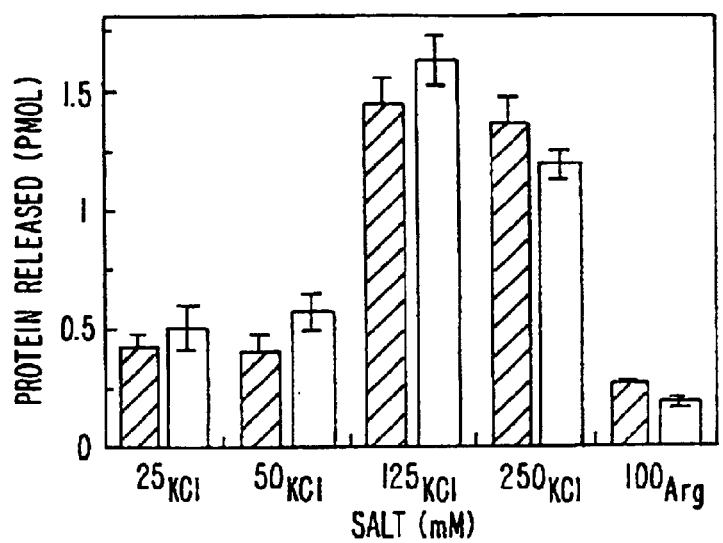
Figure 4C:
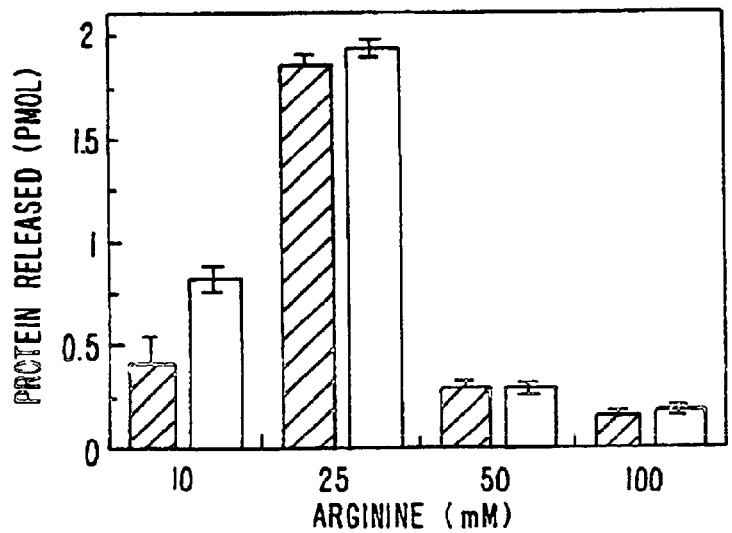

For numerous applications it is important to immobilize proteins under physiological conditions. Enzymes, for example, often need the presence of $Mg^{2+}$ ions and $K^+$ ions for maximum catalytic activity. The compatibility of this immobilization strategy with these ions was tested and the result is shown in FIG. 4. Multiple washing steps with increasing concentrations of $MgCl_2$, followed by a final arginine wash revealed the same release characteristics caused by NaCl (FIG. 3). The location of the Arg-tag on either the C-terminus or the N-terminus of the protein had no influence on the interaction with the mica. In addition, the slightly hidden position of the Arg-tag of GFPH6R6 did not decrease its binding efficiency compared to GFPR6.

The monovalent cation $K^+$ is similar to arginine in its ability to release the GFPH6R6 and the GFPR6 from the mica substrate, although higher concentrations are necessary. Potassium is the naturally occurring cation in muscovite mica and has a lower enthalpy of hydration than sodium, explaining its "power" for inducing Arg-tagged GFP desorption from the mica.

These experiments demonstrate that GFP with an Arg-tag on one of its termini can be reversibly and specifically bound via this sequence onto the mica surface.

Figure 5A:
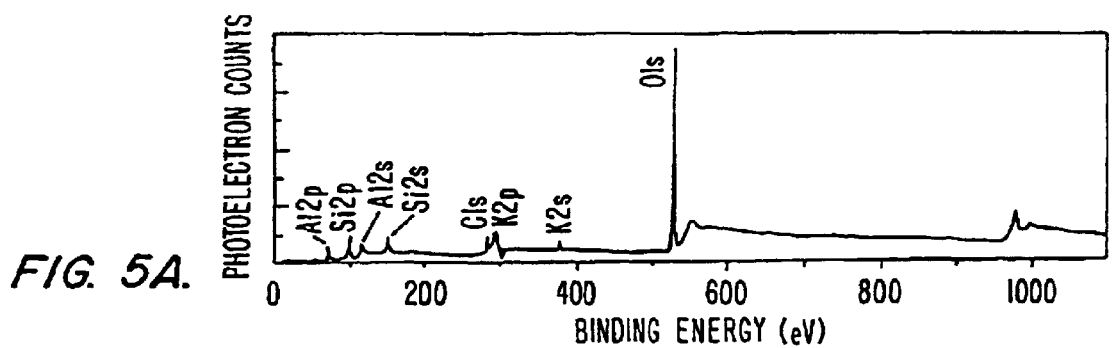
FIG. 5 shows XPS-survey spectra of (A) freshly cleaved mica and (B) GFPR6 immobilized to mica. The binding strength of bound GFPR6 ((C) and (E)), and of bound GFPH3 (D) to mica after washing with increasing amounts of NaCl and KCl is shown as monitored by the XPS N1s narrow scans (arbitrary units and normalized to the Si1s signal). The dashed line means no photoelectron counts.
Figure 5B:
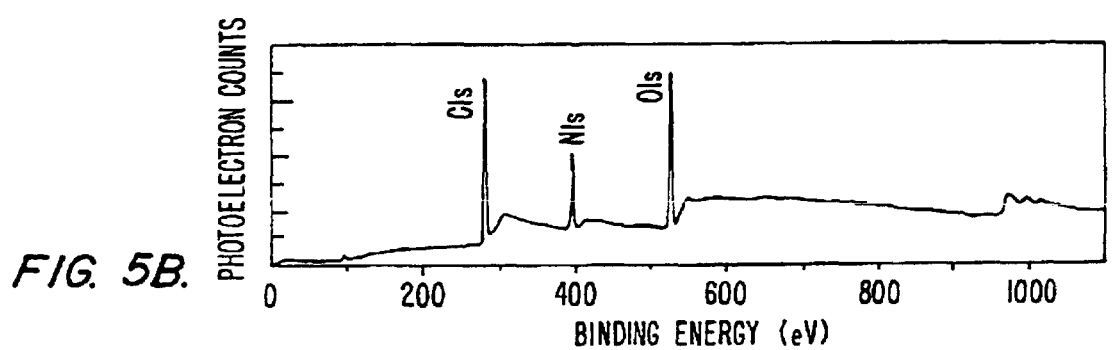

In order to investigate the complete release of protein from the mica surface after these washing steps, the mica was examined with XPS. The XPS spectrum of freshly cleaved mica as shown in FIG. 5A exhibits the corresponding peaks for aluminum (A12p (73.1 eV), A12s (118.2 eV)), silicon (Si2p (101.4 eV), Si2s (152.2 eV)), potassium (K2p (292.9 eV), K2s (377.8 eV)) and oxygen (O1s (532.0 eV). All these elements are constituent components of the mica silica structure (the very small carbon peak (C1s) at 284.6 eV is due to contaminations from the environment). After adsorption of GFPR6 (see FIG. 5B), the XPS spectrum changes considerably towards increased carbon (C1s (284.6 eV), oxygen (531.8 eV), and nitrogen (N1s, 399.6 eV) peaks. Due to the thickness of the protein film, the signals for the silicon and aluminum peaks disappear into the noise level.

Figures 5C, 5D, 5E:
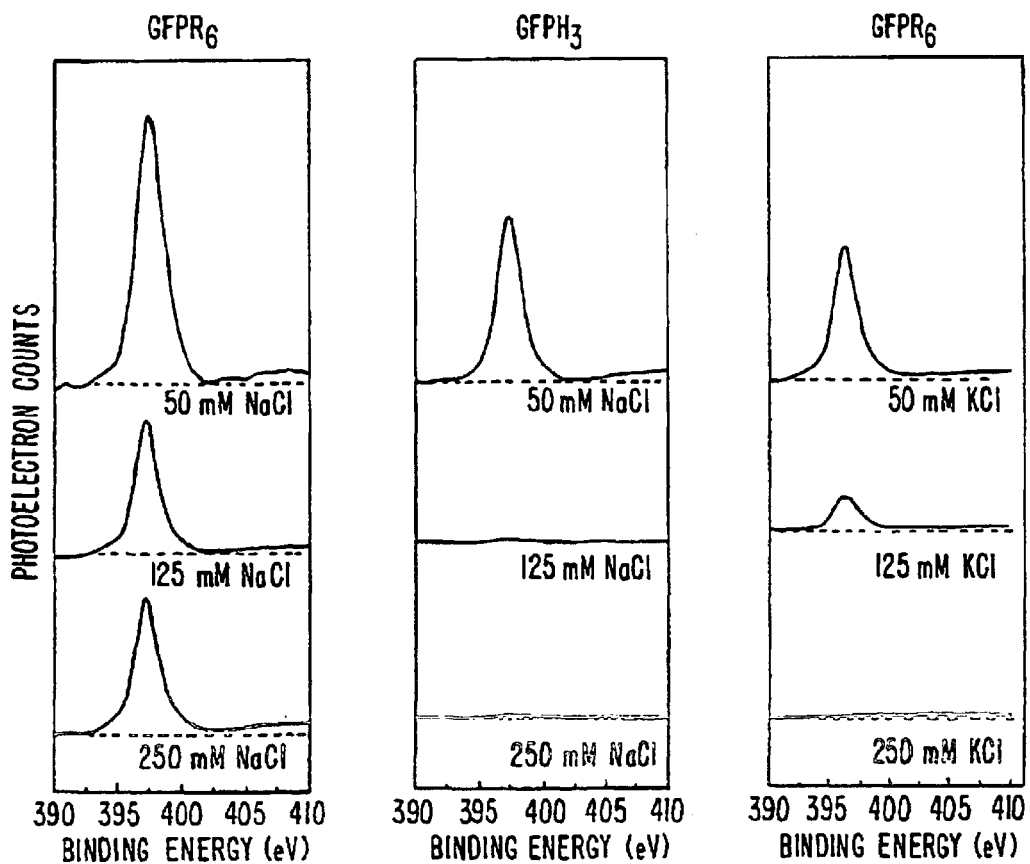

The survey spectra of GFPH6R6 and GFPH6 are nearly identical, although the latter shows less amounts of bound protein after rinsing with water (data not shown). The detection of nitrogen on the surface and its removal upon protein desorption under different buffer conditions is shown in FIG. 5C with N1s narrow scans. Whereas the Arg-tagged GFPR6 showed a similar decrease by a factor of two, as shown before by fluorescence (FIG. 3), GFPH6 lacking the Arg-tag was washed off completely at 125 mM NaCl.

In order to rule out irreversible attachment of GFPR6, a similar experiment was carried out with KCl mediated desorption as shown in the right panel of FIG. 5C, demonstrating that at very high KCl concentrations (250 mM) no protein was detectable. These results are consistent with the fluorescence measurement (FIG. 3) and clearly indicate that GFPR6 binds reversibly via its Arg-tag and without denaturation. Considering that the GFP is a cylinder with a height of 4–5 nm and a diameter of 3–4 mn [Yang et al. (1996) *Nature Biotechnology*, 14: 1246–1251], a 1 $cm^2$ area of mica could theoretically bind 6–8 pmol GFP in a densely packed monolayer. The added amounts of desorbed Arg-tagged protein after consecutive washing steps with increasing salt concentrations and finally arginine correspond to 3–4 pmol (as estimated from the sum of the bars in FIGS. 3 and 4). As described above, XPS showed that the consecutive washes shown in FIG. 3 and 4 led to the complete release of all protein bound (FIG. 5). This suggests that GFP forms a noncrystalline, but densely packed, protein monolayer on the mica surface.

The fact that the desorbed protein was still fluorescent demonstrates that adsorption and desorption did not disrupt the native structure of the protein.

An analogous set of experiments was carried out with glutathione-S-transferase and obtained the identical Arg-tag mediated binding behavior (data not shown). This strongly indicates that Arg-tag fusion proteins could be of general applicability, even for larger proteins. In each case, the maximum ionic strength must be determined and adjusted in order to minimize random, nonspecific electrostatic interactions of the target protein and to achieve an attachment situation where the protein is only bound via its Arg-tag. It is likely that proteins immobilized in this way exhibit uniform orientation. The fact that mica is atomically flat could help to investigate the structure of uniformly oriented biomolecules by electron and scanning probe microscopy and other surface-related biophysical assays. It should be noted, however, that the charge distribution on the surface of a protein of interest could influence its adsorption properties. Patches of arg-rich areas could act as additional adsorption sites and jeopardize any attempts to achieve uniform orientation.

The stability of immobilized Arg-tagged proteins allows functional studies under physiological conditions and even at high ionic strength. In many cases, proteins lacking the polyarginine sequence should not bind at such high salt concentrations, which could also facilitate in situ purification directly on the mica substrate.

This concept should be widely applicable to a large number of proteins and represents a powerful strategy to design anisotropic protein surfaces for applications in structural biology, biosensing and biophysics.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference.

---

What is claimed is:

1. A method of attaching a protein to a surface of a layered silicate, said method comprising the steps of:
   covalently attaching said protein to an arginine tag, and contacting said arginine tag with said surface of said layered silicate, wherein said protein is selected from the group consisting of a DNA binding protein, a molecular motor, an actin filament, a microtubule, a myosin filament, an actin binding protein, and a myosin filament binding protein.

2. The method of claim 1, wherein said arginine tag comprises at least two arginine residues.

3. The method of claim 1, wherein said arginine tag comprises from two to 100 arginine residues.

4. The method of claim 1, wherein said arginine tag consists of arginine residues.

5. The method of claim 1, wherein said layered silicate comprises mica.

6. The method of claim 1, wherein said method further comprises contacting said surface of said layered silicate with a solution comprising a sodium salt in a concentration sufficient to remove said arginine tag that is bound to said surface of said layered silicate by non-specific ion exchange.

7. The method of claim 6, wherein said sodium salt is present in a concentration of at least 1 mM.

8. The method of claim 1, wherein said layered silicate is chosen from one or more of vermiculite, montmorillonite, bentonite, hectorite, fluorohectorite, hydroxyl hectorite, muscovite boron fluorophlogopite, hydroxyl boron phlogopite, and mica.

9. The method of claim 1, wherein said arginine tag comprises a homopolymer consisting of 6 contiguous arginine residues.

* * * * *

UNITED STATES PATENT AND TRADEMARK OFFICE
CERTIFICATE OF CORRECTION

PATENT NO. : 6,960,457 B1
APPLICATION NO. : 09/486480
DATED : November 1, 2005
INVENTOR(S) : Spudich et al.

Page 1 of 1

It is certified that error appears in the above-identified patent and that said Letters Patent is hereby corrected as shown below:

Column 1:

• Please replace lines 14-22 with:

--FEDERALLY-SPONSORED RESEARCH OR DEVELOPMENT
This invention was made with Government support under contracts GM040509 and GM033289 awarded by the National Institutes of Health. The Government has certain rights in this invention.--

Signed and Sealed this
Nineteenth Day of April, 2011

David J. Kappos
*Director of the United States Patent and Trademark Office*

SEQUENCE LISTING

<160> NUMBER OF SEQ ID NOS: 9

<210> SEQ ID NO 1
<211> LENGTH: 34
<212> TYPE: DNA
<213> ORGANISM: Artificial Sequence
<220> FEATURE:
<223> OTHER INFORMATION: Synthetic

<400> SEQUENCE: 1
ggaattccat atgagtaaag gagaagaact tttc                              34

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
gaccggcgct cagttggaat tc                                           22

<210> SEQ ID NO 3
<211> LENGTH: 58
<212> TYPE: DNA
<213> ORGANISM: Artificial Sequence
<220> FEATURE:
<223> OTHER INFORMATION: Synthetic

<400> SEQUENCE: 3
ttggaattca ttagcgacgg cgacggcgac gcgggtgcct ttgtagagct catccatg    58

<210> SEQ ID NO 4
<211> LENGTH: 55
<212> TYPE: DNA
<213> ORGANISM: Artificial Sequence
<220> FEATURE:
<223> OTHER INFORMATION: Synthetic

<400> SEQUENCE: 4
ggaattccat atgcgccgtc gccgtcgccg tatgagtaaa ggagaagaac ttttc       55

<210> SEQ ID NO 5
<211> LENGTH: 20
<212> TYPE: PRT
<213> ORGANISM: Artificial Sequence
<220> FEATURE:
<223> OTHER INFORMATION: Synthetic

<400> SEQUENCE: 5

Met Gly Ser Ser His His His His His His Ser Ser Gly Leu Val Pro
1               5                   10                  15

Arg Gly Ser His
            20

<210> SEQ ID NO 6
<211> LENGTH: 26
<212> TYPE: PRT
<213> ORGANISM: Artificial Sequence -continued

```
<220> FEATURE:
<223> OTHER INFORMATION: Synthetic

<400> SEQUENCE: 6

Met Gly Ser Ser His His His His His Ser Ser Gly Leu Val Pro
1               5                   10                  15

Arg Gly Ser Arg Arg Arg Arg Arg His
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: NON_CONS
<222> LOCATION: (20)..(21)
<223> OTHER INFORMATION:

<400> SEQUENCE: 7

Met Gly Ser Ser His His His His His Ser Ser Gly Leu Val Pro
1               5                   10                  15

Arg Gly Ser His Gly Thr Ala Arg Arg Arg Arg Arg
            20                  25

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Arg Arg Arg Arg Arg Arg
1               5

<210> SEQ ID NO 9
<211> LENGTH: 59
<212> TYPE: DNA
<213> ORGANISM: Artificial Sequence
<220> FEATURE:
<223> OTHER INFORMATION: Synthetic

<400> SEQUENCE: 9
ttggaattca ttagcgacgg cgacggcgac gcgcggtgcc tttgtagagc tcatccatg      59
```